US010907212B2

(12) United States Patent
Skubitz et al.

(10) Patent No.: US 10,907,212 B2
(45) Date of Patent: Feb. 2, 2021

(54) INHIBITORS OF CELL ADHESION

(71) Applicant: Regents of the University of Minnesota, Minneapolis, MN (US)

(72) Inventors: Amy P. Skubitz, Edina, MN (US); Kristin L. M. Boylan, St. Paul, MN (US); Petra Buchanan, Minneapolis, MN (US); Rory Manion, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 72 days.

(21) Appl. No.: 15/595,604

(22) Filed: May 15, 2017

(65) Prior Publication Data

US 2017/0335404 A1 Nov. 23, 2017

Related U.S. Application Data

(60) Provisional application No. 62/336,619, filed on May 14, 2016.

(51) Int. Cl.
| | | |
|---|---|---|
| *C12Q 1/68* | (2018.01) | |
| *C07K 14/705* | (2006.01) | |
| *C12N 15/113* | (2010.01) | |
| *G01N 33/574* | (2006.01) | |
| *A61K 38/04* | (2006.01) | |
| *A61P 35/00* | (2006.01) | |
| *C12Q 1/6886* | (2018.01) | |

(52) U.S. Cl.
CPC ...... *C12Q 1/6886* (2013.01); *C07K 14/70503* (2013.01); *C12N 15/1138* (2013.01); *G01N 33/574* (2013.01); *C12N 2310/14* (2013.01); *C12N 2310/531* (2013.01); *C12Q 2600/118* (2013.01); *C12Q 2600/136* (2013.01); *C12Q 2600/158* (2013.01); *G01N 2333/705* (2013.01)

(58) Field of Classification Search
CPC ............ C12Q 1/6886; C12Q 2600/118; C12Q 2600/136; C12Q 2600/158; C07K 14/70503; C12N 15/1138; C12N 2310/14; C12N 2310/531; G01N 33/574; G01N 2333/705

See application file for complete search history.

(56) References Cited

U.S. PATENT DOCUMENTS

| | | | | |
|---|---|---|---|---|
| 5,837,218 A | * | 11/1998 | Peers | A61K 51/088 424/1.69 |
| 6,641,818 B1 | * | 11/2003 | Spear | C07K 14/005 424/204.1 |

FOREIGN PATENT DOCUMENTS

AU 2008202217 A9 * 6/2008

OTHER PUBLICATIONS

Panneerselvam et al, IL-24 Inhibits Lung Cancer Cell Migration and Invasion by Disrupting the SDF-1/CXCR4 Signaling Axis, PLoS One, 2015, 10, pp. 1-22.*
Bojesen et al, Nectin-1 Binds and Signals through the Fibroblast Growth Factor Receptor, The Journal of Biological Chemistry, 2012, 287, pp. 37420-37433.*
Linseman et al, Suppression of Death Receptor Signaling in Cerebellar Purkinje Neurons Protects Neighboring Granule Neurons from Apoptosis via an Insulin-like Growth Factor I-dependent Mechanism, The Journal of Biological Chemistry, 2002, 277, pp. 24546-24553.*
Boylan, Kristin L. M., et al., "The expression of Nectin-4 on the surface of ovarian cancer cells alters their ability to adhere, migrate, aggregate, and proliferate", Oncotarget, 8(6), (2017), 9717-9738.
Buchanan, Petra C., et al., "Ecodomain shedding of the cell adhesion molecule Nectin-4 in ovarian cancer is mediated by ADAM10 and ADAM17", JBC Papers in Press. Published on Feb. 23, 2017 as Manuscript M116.746859 (Journal of Biological Chemistry, 292, (2017), 6339-6351), (2017), 25 pgs.
Challita-Eid, Pia M., et al., "Enfortunab Vedotin Antibody-Drug Conjugate Targeting Nectin-4 Is a Highly Potent Therapeutic Agen in Multiple Preclinical Cancer Models", Cancerres.aacrjournais.org on May 5, 2016. 2016 American Association for Cancer Research, Published Online First Mar. 24, 2016; DOI: 10.115810008-5472, CAN-15/1313, (2016), 12.
Fabre-Lafay, Stephanie, et al., "Nectin-4 is a new histological and serological tumor associated marker for breast cancer", BMC Cancer, 7:73, (2007), 16 pgs.
Campbell, Dean O., et al., "Preclinical Evaluation of an Anti-Nectin-4 ImmunoPET Reagent in Tumor-Bearing Mice and Biodistribution Studies in Cynomolgus Monkeys", *Mol. Imaging Biol.*, 18, (2016), 768-775.
M-Rabet, M., et al., "Nectin-4: a new prognostic biomarker for efficient therapeutic targeting of primary and metastatic triple-negative breast cancer", *Annals of Oncology*, 28(4), (2017), 769-776.
Boylan, Kristin L.M., et al., "Inhibition of Ovarian Cancer Cell Spheroid Formation by Synthetic Peptides Derived from Nextin-4", International Journal of Molecular Sciences, 2020, 21, 4637, (2020), 1-16.

* cited by examiner

*Primary Examiner* — Li N Komatsu
(74) *Attorney, Agent, or Firm* — Schwegman Lundberg & Woessner, P.A.

(57) ABSTRACT

Nectin-4 and Nectin-1 in cancer progression/development and as a therapeutic target for cancer.

10 Claims, 13 Drawing Sheets

Specification includes a Sequence Listing.

INHIBITORS OF CELL ADHESION

PRIORITY

This application claims the benefit of priority from U.S. Provisional Patent Application Ser. No. 62/336,619, filed on May 14, 2016, which is herein incorporated by reference.

BACKGROUND OF THE INVENTION

Ovarian cancer is the most lethal gynecological malignancy, resulting in over 14,000 deaths annually in the U.S. [1]. Due to the vague symptoms and lack of a screening test suitable for the general population, most women are diagnosed at a late stage of disease, when patients have a poor prognosis. Although most ovarian cancer patients will respond to initial treatment with surgery and chemotherapy, the majority relapse with chemoresistant disease [2].

SUMMARY OF THE INVENTION

Many cancers have cells that metastasize to other sites. They may use cell-cell adhesion to adhere to other sites or form cell-cell aggregates that are resistant to chemotherapy (chemotherapy is used to kill individual cancer cells, but cell-cell aggregates (spheroids) are resistant to many chemotherapies). By blocking these adhesions with peptides of the invention, it may be possible to limit or block cancer metastasis (adhesions/spheroid formation). Provided herein are novel nectin peptides that can functionally block cell adhesion.

One embodiment provides a peptide having an amino acid sequence of N4-P1 to N4-P29 (SEQ ID NOs: 5-31, 59 and 60), N1-P1 to N1-P28 (SEQ ID NOs: 32-58 and 61) or modifications thereof. In one embodiment, the peptide is N4-P10, N4-P18, N4-P22, N4-P29, N1-P1, N1-P17, N1-P20 or N1-P26 or modifications thereof.

One embodiment provides a composition comprising at least one peptide of the invention and a physiologically acceptable carrier. For example, the composition can comprises 1, 2, 3, 4, 5, 6, 7, 8, 9, 10 peptides of the invention and so. In one example, the composition provides at least 5 peptides of the invention (for example, in a vaccine to stimulate the immune system of patients, such as T cells of patients).

Another embodiment provides a method to inhibit cell adhesion of a cancer cell comprising contacting said cancer cell with an effective amount of at least one peptide of the invention or a composition comprising at least one peptide of the invention so as to inhibit cell adhesion of the cancer cell.

One embodiment provides a method to inhibit cell migration, spheroid formation, cell invasion, and/or cell proliferation of a cancer cell comprising contacting said cancer cell with an effective amount of at least one peptide of the invention or a composition comprising at least one peptide of the invention so as to inhibit cell migration, spheroid formation, cell invasion, and/or cell proliferation of the cancer cell.

Another embodiment provides a method to inhibit cell adhesion of a cancer cell comprising administering to a subject in need therefore an effective amount of at least one peptide of the invention or a composition comprising at least one peptide of the invention so as to inhibit cell adhesion of the cancer cell in said subject.

One embodiment provides a method to treat cancer comprising administering to a subject in need therefore an effective amount of at least one peptide of the invention or a composition comprising at least one peptide of the invention so as to treat the cancer in said subject.

One embodiment provides a method to treat cell-cell adhesions comprising administering to a subject in need therefore an effective amount of at least one peptide of the invention or a composition comprising at least one peptide of the invention so as to treat the cell-cell adhesions in said subject. In one embodiment, the cell-cell adhesions are intraperitoneal adhesions following surgery.

In one embodiment, the cancer cell or cancer is selected from the group consisting of carcinoma (e.g., head and neck squamous cell carcinoma), sarcoma, uterine cancer, ovarian cancer, lung cancer, adenocarcinoma, adenocarcinoma of the lung, squamous carcinoma, squamous carcinoma of the lung, malignant mixed mullerian tumor, leukemia, lymphoma, neuroblastoma, melanoma, breast cancer, prostate cancer, pancreatic cancer, kidney cancer, bladder and endometrioid carcinoma.

In one embodiment, the cancer cell or cancer is ovarian.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 12A-B Provide a summary of peptide, binding assay data (binding, flow and spheroid formation) for Nectin-4 (A) and Nectin-1 (B).

DETAILED DESCRIPTION OF THE INVENTION

Figure 1:
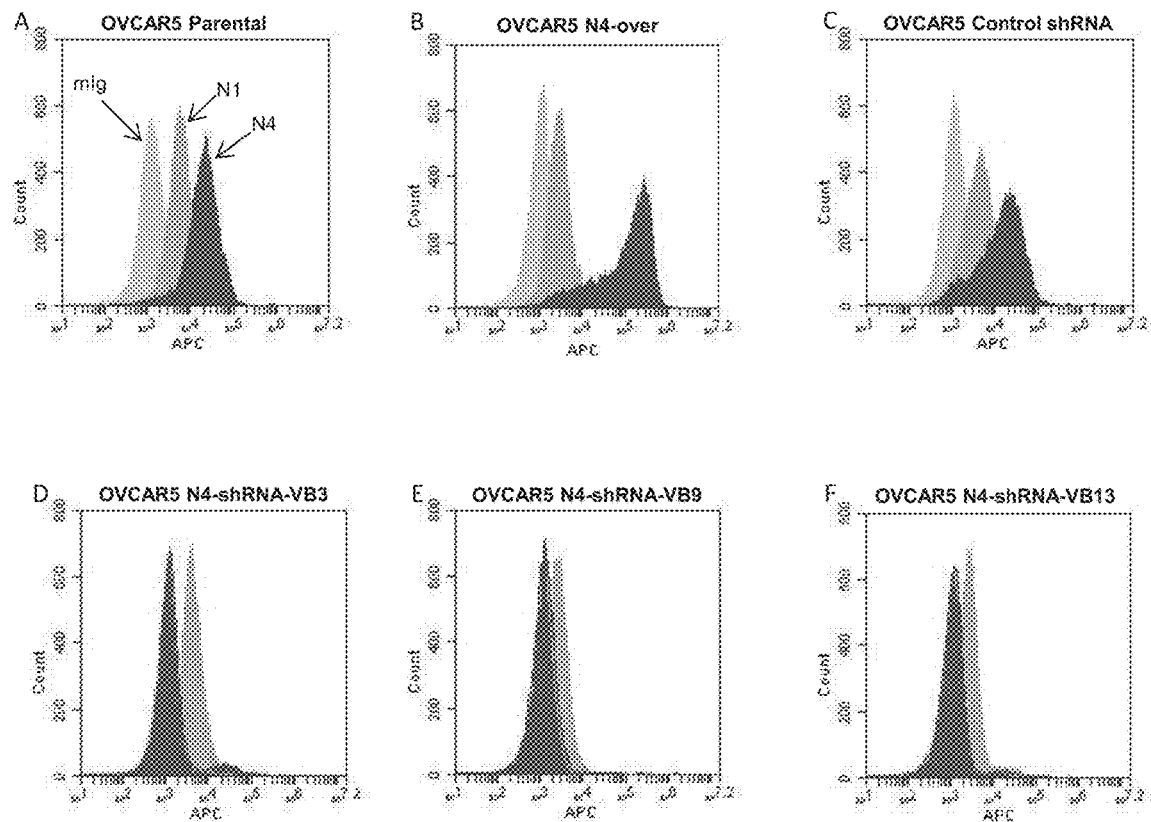
FIGS. 1A-F Flow cytometric analysis of NIH:OVCAR5 cells for expression of Nectin-4 and Nectin-1. Cells were analyzed by flow cytometry for the expression of Nectin-4, Nectin-1 or mouse IgG negative control (mIg). Cells tested were: (A) NIH:OVCAR5 parental cells; (B) NIH:OVCAR5 over expressing Nectin-4; and (C) NIH:OVCAR5 stably expressing control shRNA. Single cell clones of NIH:OVCAR5 cells stably expressing Nectin-4 shRNA: (D) VB3, (E) VB9, and (F) VB13.

The cell adhesion molecule Nectin-4 is overexpressed in numerous epithelial cancers, including ovarian cancer. Provided herein is a determination of the role that Nectin-4 plays in the adhesion, aggregation, migration, and proliferation of ovarian cancer. Assays were conducted using the human NIH:OVCAR5 cell line that was genetically modified to either knock-down Nectin-4 expression with shRNA targeting Nectin-4, or overexpress a full-length Nectin-4 construct. Cells that overexpressed Nectin-4 adhered to Nectin-1 in a concentration and time-dependent manner, and cell adhesion was inhibited by antibodies to Nectin-4 and Nectin-1. Synthetic peptides from Nectin-4 and Nectin-1 were used to localize the sites that are involved in cell adhesion. Several IgC domain peptides inhibited cell adhesion by 50%, and one peptide from Nectin-1 almost completely abrogated cell adhesion. Cells expressing Nectin-4 formed multicellular aggregates (spheroids) that were over two-fold larger than cells in which Nectin-4 expression was knocked down. Cells that expressed Nectin-4 also migrated more rapidly and proliferated nearly twice as fast as Nectin-4 knock-down cells. The results demonstrate that Nectin-4 promotes cell-cell adhesion (involved in the formation of spheroids), cell migration, and proliferation. Understanding the biology of Nectin-4 in ovarian cancer progression facilitates its development as a novel therapeutic target for ovarian cancer.

For the purposes of clarity and a concise description, features can be described herein as part of the same or separate embodiments; however it will be appreciated that the scope of the invention may include embodiments having combinations of all or some of the features described herein.

The terminology used herein is for the purpose of describing particular embodiments only and is not intended to be limiting of the invention.

As used herein, the indefinite articles "a", "an" and "the" should be understood to include plural reference unless the context clearly indicates otherwise.

The phrase "and/or," as used herein, should be understood to mean "either or both" of the elements so conjoined, e.g., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology. Peptides provided for herein are at least 50%, 60%, 70%, 80%, 90%, 95%, 96%, 97%, 98%, 99% or 100% identical to those provide for in Table I.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

As used herein, the term "subject" refers to any animal (e.g., mammals, birds, reptiles, amphibians, fish), including, but not limited to, humans, non-human primates, rodents, and the like, which is to be the recipient of a particular treatment. Typically, the terms "subject" and "patient" may be used interchangeably herein in reference to a subject.

The term "biological sample," as used herein, refers to samples obtained from a subject, including, but not limited to, skin, hair, tissue, blood, plasma, cells (including cancer and non-cancerous cells (e.g., control cells)), sweat and/or urine.

"Treating" means either slowing, stopping, inhibiting or reversing the progression of a disease or disorder. As used herein, "treating" also means the amelioration of symptoms associated with the disease or disorder.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

A. Peptides

This invention provides a peptide for use in treating cancer and/or inhibiting cell adhesion. (In fact, molecules that block the activity/binding of Nectin can be used, for example, enfortumab vedotin antibody-drug conjugate as described in Challita-Eid et al. Cancer Res; 76(10) May 15, 2016 (epub on Mar. 24, 2016).) The amino acid sequences of the peptides are provided in Table 1. A series of 29 Nectin-4 peptides and 28 Nectin-1 peptides were generated. Peptides were found to inhibit cancer cell adhesion to Nectin (e.g., -1 and -4), such as ovarian cancer cells. The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified. "Polypeptide" or "peptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Amino acid," "amino acid residue" and "residue" are used interchangeably herein to refer to an amino acid that is incorporated into a protein, polypeptide or peptide. The amino acid can be, for example, a naturally occurring amino acid or an analog of a natural amino acid that can function in a manner similar to that of the naturally occurring amino acid.

Amino acids have the following general structure:

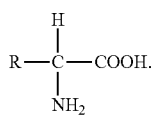

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp The term "peptide" typically refers to short polypeptides.

The term "basic" or "positively charged" amino acid as used herein, refers to amino acids in which the R groups have a net positive charge at pH 7.0, and include, but are not limited to, the standard amino acids lysine, arginine, and histidine.

Also are included fragments of the polypeptides such as "biologically active fragments" or "bioactive fragment" of the polypeptides which encompasses natural or synthetic portions of the full length protein that are capable of specific binding to their natural ligand or of performing the function of the protein.

The peptides of the present invention may be readily prepared by recombinant techniques as well as by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method that utilized tert-butyloxycarbonyl as the α-amino protecting group, and the FMOC method which utilizes 9-fluorenylmethyloxycarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

i. Amino Acid Substitutions and Amino Acid/Peptide Modifications

In certain embodiments, the disclosed methods and compositions may involve preparing peptides with one or more substituted amino acid residues, such as conservative substitutions as discussed above. For example, in various embodiments, the structural, physical and/or therapeutic characteristics of peptide sequences may be optimized by replacing one or more amino acid residues.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2', -3', - or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Peptides described herein can also include non-natural amino acids are non-proteinogenic amino acids, such as, β-amino acids (β3 and β2), homo-amino acids, proline and pyruvic acid derivatives, 3-substituted Alanine derivatives, glycine derivatives, ring-substituted phenylalanine and tyrosine derivatives, linear core amino acids, N-methyl amino acids, heavy atom containing amino acids and/or L- and D-amino acids (in protected or unprotected forms). Such non-natural amino acids can be used to, for example, increase half-life, activity and/or solubility. The peptides can also include probes and/or tags.

Possible chemical modifications of the protein moieties of the present invention also include derivitization with polyethylene glycol (PEG) or other polymers (such as dextran) to extend time of residence in the circulatory system and reduce immunogenicity, according to well-known methods (See for example, Lisi, et al., Applied Biochem. 4:19 (1982); Beauchamp, et al., Anal Biochem. 131:25 (1982); and Goodson, et al., Bio/Technology 8:343 (1990)).

It may also be advantageous to add to the amino- or carboxy-terminus of the peptide chemical moieties or additional (modified or D-) amino acids in order to increase the stability and/or decrease the biodegradability of the peptide.

A peptide bond mimetic of the invention includes peptide backbone modifications well known to those skilled in the art. Such modifications include modifications of the amide nitrogen, the alpha carbon, amide carbonyl, complete replacement of the amide bond, extensions, deletions, or backbone cross-links. See, generally, Spatola, Chemistry and Biochemistry of Amino Acids, Peptides and Proteins, Vol. VII (Weinstein ed., 1983). Several peptide backbone modifications are known and can be used in the practice of the invention.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include C1-C5 branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—NH2), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without effect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

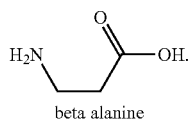

beta alanine

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

B. Treat Disease/Symptom

This invention provides a method for inhibiting adhesion and/or treating a subject having cancer or a cell adhesion related disorder comprising administering to the subject an amount of one or more of the above described peptides or modified peptides effective to treat the subject. The term "cancer", as used herein, is defined as proliferation of cells whose unique trait—loss of normal controls—results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer. For example, this invention provides a method for treating a subject having ovarian cancer comprising administering to the subject an amount of one or more of the above peptides effective to treat the subject, thereby treating the subject having ovarian cancer.

C. Administer

This invention provides use of one or more of the above peptides or modified peptides for the preparation of a pharmaceutical composition for the treatment of a subject having cancer or a cell adhesion related disorder. This invention provides use of one or more of the above peptides or modified peptides for the preparation of a pharmaceutical composition for treating a subject having ovarian cancer.

The present invention also relates to a pharmaceutical composition comprising peptides of the present invention in a pharmaceutically acceptable carrier. In therapeutic applications, compositions are administered to a patient suffering from a disease, in an amount sufficient to cure or at least partially arrest the disease and its complications. An amount adequate to accomplish this is defined as a therapeutically effective dose. Amounts effective for this use will depend on the severity of the disease and the general state of the patient's health.

As used herein, the term "composition", as in pharmaceutical composition, is intended to encompass a product comprising the active ingredient(s) and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Administering" may be effected or performed using any of the methods known to one skilled in the art. The methods comprise, for example, intralesional, intramuscular, subcutaneous, intravenous, intraperitoneal, liposome-mediated, transmucosal, intestinal, topical, nasal, oral, anal, ocular or otic means of delivery.

As used herein, the term "administering" refers to providing a therapeutically effective amount of a chemical or biological compound or pharmaceutical composition to a subject. The chemical or biological compound of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; ear drops; sprays, including nasal sprays; other proteins and peptides; synthetic polymers; microspheres; nanoparticles; and the like.

Advantageously, the pharmaceutical composition is suitable for parenteral administration. Single or multiple administrations of the compositions may be administered depending on the dosage and frequency as required and tolerated by the patient. In any event, the composition should provide a sufficient quantity of the peptides of this invention to effectively treat the patient.

As used herein, "effective amount" refers to an amount which is capable of treating a subject having a tumor, a disease or a disorder. Accordingly, the effective amount will vary with the subject being treated, as well as the condition to be treated. A person of ordinary skill in the art can perform routine titration experiments to determine such sufficient amount. The effective amount of a compound will vary depending on the subject and upon the particular route of administration used. Based upon the compound, the amount can be delivered continuously, such as by continuous pump, or at periodic intervals (for example, on one or more separate occasions). Desired time intervals of multiple amounts of a particular compound can be determined without undue experimentation by one skilled in the art. In one embodiment, the effective amount is between about 1 µg/kg-10 mg/kg. In another embodiment, the effective amount is between about 10 µg/kg-1 mg/kg. In a further embodiment, the effective amount is 100 µg/kg.

The compositions for administration will commonly comprise a solution of the peptide in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

The peptides of this invention may be administered systemically by injection, such as intravenously, but also intramuscularly, subcutaneously, intrathecally, intraperitoneally, into vascular spaces, or into joints, e.g., intraarticular injection. In one embodiment, the invention provides a method of treating a subject by administering compounds identified using the methods of the invention description. Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means. The dose will be dependent upon the properties of the peptides employed, e.g., its activity and biological half-life, the concentration of the peptide in the formulation, the site and rate of dosage, the clinical tolerance of the patient involved, the extent of cancer afflicting the patient and the like as is well within the skill of the physician.

Administration may also be intranasal or by other non-parenteral routes. The peptide may also be administered via microspheres, liposomes or other microparticulate delivery systems placed in certain tissues including blood.

The peptides of the present invention may be administered in solution. The pH of the solution can be in the range of pH 5 to 9.5, such as pH 6.5 to 7.5. The peptides or derivatives thereof can be in a solution having a suitable pharmaceutically acceptable buffer such as phosphate, tris (hydroxymethyl) aminomethane-HCl or citrate and the like. Buffer concentrations should be in the range of 1 to 100 mM. The solution of the immunoglobulin can also contain a salt, such as sodium chloride or potassium chloride in a concentration of 50 to 150 mM. An effective amount of a stabilizing agent such as albumin, a globulin, a detergent, a gelatin, a protamine or a salt of protamine can also be included and can be added to a solution containing the immunotoxin or to the composition from which the solution is prepared. The peptide may be formulated with a polymer (such as polyethylene glycol (PEG) or dextran), which can be used to increase the biological half-life of the peptide, thus resulting in a more extended period of activity. Systemic administration of the peptide can be made every two to three days or once a week. Alternatively, daily administration is useful. For example, the peptide may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

In accordance with one embodiment, a method of treating a subject in need of such treatment is provided. The method comprises administering a pharmaceutical composition comprising at least one peptide of the present invention to a subject in need thereof. Peptides for use in the methods of the invention can be administered with known compounds or other medications as well.

The terms "additional therapeutically active compound" or "additional therapeutic agent," as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The invention also includes a kit comprising the composition of the invention and an instructional material which describes administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

EXAMPLES

The following examples are provided in order to demonstrate and further illustrate certain embodiments and aspects of the present invention and are not to be construed as limiting the scope thereof.

Example I

Introduction

The primary mechanism of ovarian cancer progression is by localized tumor shedding and seeding within the peritoneal cavity, although hematogenous metastasis has been observed [3]. Cells are released from the primary tumor, which may arise in the fimbria of the fallopian tube [4], and then seed throughout the peritoneal cavity, attaching to the local organs and invading, ultimately resulting in the death of the patient. Ovarian cancer cells are unique in their ability to recruit fluid into the peritoneal cavity (ascites fluid) and exist in a free-floating form as single cells and multicellular aggregates, termed spheroids. Spheroids are able to resist standard chemotherapy (which relies upon rapidly dividing cells), due to their slow replication and the protection afforded by the tight cell aggregation [5, 6]. Ovarian cancer spheroids are also capable of adhering to extracellular matrix proteins and monolayers of mesothelial cells [7-11] and can disaggregate and invade the peritoneal organs [8, 12-16].

Overexpression of the cell adhesion molecule Nectin-4 (PVRL4) in ovarian cancer tissues was discovered by gene microarray analysis [17]. Subsequently, it was shown that Nectin-4 RNA and protein are overexpressed in ovarian cancer tissues and cell lines compared to their normal ovarian counterparts [18]. More recently, in a study of 25 ovarian cancer tumors, Nabih et al [19] found that expression of Nectin-4 mRNA was increased in 97.4% of the ovarian cancer samples. Normal tissue expression of Nectin-4 is largely limited to the placenta; however, lower levels of expression are found in the skin, stomach, prostate, lung and trachea [20, 21]. It was also shown that the cleaved, soluble extracellular domain of Nectin-4 (sN4) is detectable at elevated levels in the sera of ovarian cancer patients [18]. Nectin-4 overexpression has been reported in ductal breast carcinoma, lung adenocarcinoma, and pancreatic cancer; and high Nectin-4 expression in those tumors was associated with disease progression or poor prognosis [22-26]. Several of these studies also detected elevated levels of sN4 in cancer patients' serum and, in the case of breast cancer, a correlation was shown between high levels of sN4 and number of metastases [24, 26]. Clinical trials are underway to target carcinomas that express Nectin-4 by use of a toxin-linked monoclonal antibody (mAb) against Nectin-4 [27].

Nectins are a family of four $Ca^{2+}$-independent, immunoglobulin-like cell adhesion molecules important in the formation and maintenance of adherens junctions and tight junctions [28-32]. Nectins share a similar structure: three immunoglobulin-like extracellular loops, a single transmembrane region, and a short cytoplasmic domain that binds to afadin, through which nectins are connected to the actin cytoskeleton [21, 33-35]. The extracellular domains of nectins can be proteolytically cleaved to release a soluble fragment (sN4) which may regulate cell function [25, 36-38].

Nectins function as cell adhesion molecules by first forming homo cis-dimers on the cell surface and then trans-dimers on adjacent cells in both a homophilic and heterophilic manner. The specificity of binding is different for each nectin; Nectin-4 binds to itself and Nectin-1 (PVRL1) [21, 35, 39]. Cell-cell contacts are thought to be initiated by an interaction between nectins on adjacent cells. Subsequently, the cadherin-catenin complex is recruited to sites of nectin-based intercellular adhesion and the trans-interaction of cadherins on adjacent cells occurs, forming the adherens junction [28, 40].

The extracellular domains of some members of the nectin family bind to growth factors receptors, such as fibroblast growth factor receptor, platelet-derived growth factor receptor, or epidermal growth factor receptor (ERBB3/HER3), which may play a role in the regulation of nectin function in cell proliferation, migration and apoptosis [41-48]. However, the role of Nectin-4 in cellular functions, beyond cell-cell adhesion, is not well understood. A recent study by Pavlova et al. [49] provided evidence that Nectin-4 promotes anchorage independence in breast cancer cells.

Described herein is the role that Nectin-4 plays in several cellular functions that underlie ovarian cancer progression: cell adhesion, spheroid formation, migration, and proliferation. These experiments offer insight into how ovarian cancer cells act in vivo and provide a rationale for the use of agents that target Nectin-4 in a clinical setting.

Materials and Methods

Cell Culture.

The NIH:OVCAR5 human ovarian cancer cell line [58] was received from Judah Folkman (Harvard University) in 1995 and viably stored in liquid nitrogen. After thawing, cells were grown in complete medium [RPMI 1640 media containing 10% fetal bovine serum (FBS)] at 37° C. in a humidified incubator with 5% $CO_2$. The cell line was verified by short tandem repeat fingerprinting (MD Anderson Characterized Cell Line Core Facility, Houston, Tex.).

Antibodies.

Mouse monoclonal antibodies (mAb) against human Nectin-4 were purchased from Millipore (Billerica, Mass.) (MABT64, clone N4.61) and R&D Systems (Minneapolis, Minn.) (MAB2659, clone #337516). A mouse mAb against human Nectin-1 (MAB2880, clone #610835) was purchased from R&D Systems. Negative control antibodies included a mouse mAb IgG2b (MAB0041, Clone #133303, R&D Systems), a mouse mAb IgG2a (MAB003, Clone #20102, R&D Systems), and a polyclonal mouse IgG (ab37355; Abcam, Cambridge, Mass.).

Flow Cytometry.

Confluent monolayers of cells were detached from 75 cm$^2$ tissue culture flasks using Accutase cell dissociation buffer (Innovative Cell Technologies, San Diego, Calif.), washed, and labeled with mouse IgG or mAbs against Nectin-4 or Nectin-1 (2.5 µg/10$^6$ cells) in Flow Buffer [phosphate buffered saline (PBS) containing 2.5% newborn calf serum and 0.02% sodium azide] for 30 min at 4° C. [18]. Cells were washed and incubated with goat anti-mouse IgG F(ab')2 (Jackson ImmunoResearch, West Grove, Pa.), then washed again and incubated with streptavidin-allophycocyanin conjugate (Jackson ImmunoResearch, West Grove, Pa.) for 30 min each. Cells were washed and fixed in Flow Buffer containing 1% formaldehyde and analyzed in the University of Minnesota Flow Cytometry Resource with a BD Accuri™ C6 flow cytometer (BD Biosciences, San Jose, Calif.) using the Accuri™ software.

Reverse Transcription—Polymerase Chain Reaction (RT-PCR).

Total cellular RNA was isolated from cell lines using the RNeasy Mini kit (Qiagen; Hilden, Germany) per manufacturer's instructions. 100 ng of total RNA was amplified using the Access RT-PCR System (Promega Corporation, Madison, Wis.), which uses AMV Reverse transcriptase for first strand cDNA synthesis and Tfl DNA Polymerase for subsequent DNA amplification. Primers: Nectin-4 Forward (5'-CAAAATCTGTGGCACATTGG-3'; SEQ ID NO:1) and Reverse (5'-GCTGACATGGCAGACGTAGA-3'; SEQ ID NO:2), GAPDH Control Forward (5'-ACCACAGTC-CATGCCATCAC-3'; SEQ ID NO:3) and Reverse (5'-TC-CACCACCCTGTTGCTGTA-3'; SEQ ID NO:4). Amplification products were visualized on a 1% agarose gel stained with SYBR® Gold (Invitrogen™)

Overexpression of Nectin-4.

A cDNA of the full length Nectin-4 isoform cloned in the p3XFLAG-myc-CMV-25 expression vector (Sigma-Aldrich, St. Louis, Mo.) was kindly provided by Dr. Marc Lopez (Centre de Recherché en Cancérologie de Marseille, Marseille, France). NIH:OVCAR5 cells were grown to 70% confluency and transfected using Lipofectamine® LTX and Plus™ Reagent (Invitrogen™, Grand Island, N.Y.). Cells were subsequently selected using G418/Geneticin® (Invitrogen™). Overexpression of Nectin-4 was verified by flow cytometry, and fluorescence activated cell sorting (FACS) was used to select for cells that expressed high levels of Nectin-4 compared to the parental cell line. The NIH:OVCAR5 cell line that was generated, which stably overexpressed Nectin-4, will be hereafter referred to as NIH:OVCAR5-N4-over.

Lentiviral Transduction.

shRNA lentiviral particles targeting human Nectin-4 or control shRNA lentiviral particles were purchased from Santa Cruz Biotechnology, Inc. (Dallas, Tex.) and used to transduce cells according to the manufacturer's instructions. NIH:OVCAR5 cells were transduced with 10-20 µl of high titer lentiviral particles in 2 µg/ml Polybrene® (hexadimethrine bromide, Sigma-Aldrich) in complete medium. Infected cells were selected with puromycin and single cell clones were derived by limiting dilution. Clones with reduced expression of Nectin-4 were detected by RT-PCR and verified by flow cytometry. Subsequent to genetic manipulation, cells were authenticated by short tandem repeat fingerprinting (MD Anderson).

Synthetic Peptides.

Twenty-nine peptides of 14 amino acids in length were designed from the extracellular domain of Nectin-4 so that the sequences overlapped by two amino acids (Table 1). The Nectin-1 peptides synthesized ranged from 11 to 17 amino acids in length; and were selected to correspond to similar regions in Nectin-4 (Table 1). All peptides were synthesized with a free amino terminus and an amide at the carboxy terminus ($CONH_2$). The peptides were synthesized by Aapptec (Louisville, Ky.) where they were purified by high pressure chromatography, and the sequences were verified by mass spectrometry to be >95% pure. Peptides were dissolved in dimethyl sulfoxide (DMSO; Sigma-Aldrich) at a concentration of 50 mg/ml, aliquoted, and stored at −80° C.

TABLE 1

Amino acid sequences and domain localization of Nectin-4 and Nectin-1 peptides

| Nectin-4 Peptides | | | Nectin-1 Peptides | |
| --- | --- | --- | --- | --- |
| Name/ Lab ID | AA Sequence | Domain | Name/ Lab ID | AA Sequence |
| N4-P1/1 | PAGELETSDVVTVV-$NH_2$ (SEQ ID NO: 5) | IgV | N1-P1/30 | HSQVVQVNDSMYGF-$NH_2$ (SEQ ID NO: 32) |
| N4-P2/2 | VVLGQDAKLPCFYR-$NH_2$ (SEQ ID NO: 6) | IgV | N1-P2/31 | GFIGTDVVLHCSFA-$NH_2$ (SEQ ID NO: 33) |
| N4-P3/3 | YRGDSGEQVGQVAW-$NH_2$ (SEQ ID NO: 7) | IgV | N1-P3/32 | FANPLPSVKITQVTW-$NH_2$ (SEQ ID NO: 34) |
| N4-P4/4 | AWARVDAGEGAQEL-$NH_2$ (SEQ ID NO: 8) | IgV | N1-P4/33 | TWQKSTNGSKQNV-$NH_2$ (SEQ ID NO: 35) |
| N4-P5/5 | ELALLHSKYGLHVS-$NH_2$ (SEQ ID NO: 9) | IgV | N1-P5/34 | NVAIYNPSMGVSVL-$NH_2$ (SEQ ID NO: 36) |
| N4-P6/6 | VSPAYEGRVEQPPP-$NH_2$ (SEQ ID NO: 10) | IgV | N1-P6/35 | VLAPYRERVEFLRP-$NH_2$ (SEQ ID NO: 37) |
| N4-P7/7 | PPPRNPLDGSVLLR-$NH_2$ (SEQ ID NO: 11) | IgV | N1-P7/36 | RPSFTDGTIRLS-$NH_2$ (SEQ ID NO: 38) |

TABLE 1-continued

Amino acid sequences and domain localization of Nectin-4 and Nectin-1 peptides

| Nectin-4 Peptides | | | Nectin-1 Peptides | |
|---|---|---|---|---|
| Name/ Lab ID | AA Sequence | Domain | Name/ Lab ID | AA Sequence |
| N4-P8/8 | LRNAVQADEGEYEC-NH$_2$ (SEQ ID NO: 12) | IgV | N1-P8/37 | LSRLELEDEGVYIC-NH$_2$ (SEQ ID NO: 39) |
| N4-P9/9 | ECRVSTFPAGSFQA-NH$_2$ (SEQ ID NO: 13) | IgV | N1-P9/38 | ICEFATFPTGNRES-NH$_2$ (SEQ ID NO: 40) |
| N4-P10/10 | QARLRLRVLVPPLP-NH$_2$ (SEQ ID NO: 14) | IgV/IgC1 | N1-P10/39 | ESQLNLTVMAKPTN-NH$_2$ (SEQ ID NO: 41) |
| N4-P11/11 | LPSLNPGPALEEGQ-NH$_2$ (SEQ ID NO: 15) | IgC1 | N1-P11/40 | TNWIEGTQAVLRAKKGQ-NH$_2$ (SEQ ID NO: 42) |
| N4-P12/12 | GQGLTLAASCTAEG-NH$_2$ (SEQ ID NO: 16) | IgC1 | N1-P12/41 | GQDDKVLVATCTSANG-NH$_2$ (SEQ ID NO: 43) |
| N4-P13/13 | EGSPAPSVTWDTEV-NH$_2$ (SEQ ID NO: 17) | IgC1 | N1-P13/42 | NGKPPSVVSWETRL-NH$_2$ (SEQ ID NO: 44) |
| N4-P14/14 | EVKGTTSSRSFKHS-NH$_2$ (SEQ ID NO: 18) | IgC1 | N1-P14/43 | RLKGEAEYQEIRNP-NH$_2$ (SEQ ID NO: 45) |
| N4-P15/15 | HSRSAAVTSEFHLV-NH$_2$ (SEQ ID NO: 19) | IgC1 | N1-P15/44 | NPNGTVTVISRYRLV-NH$_2$ (SEQ ID NO: 46) |
| N4-P16/16 | LVPSRSMNGQPLTC-NH$_2$ (SEQ ID NO: 20) | IgC1 | N1-P16/45 | LVPSREAHQQSLAC-NH$_2$ (SEQ ID NO: 47) |
| N4-P17/17 | TCVVSHPGLLQDQR-NH$_2$ (SEQ ID NO: 21) | IgC1 | N1-P17/46 | ACIVNYHMDRFKES-NH$_2$ (SEQ ID NO: 48) |
| N4-P18/18 | QRITHILHVSFLAE-NH$_2$ (SEQ ID NO: 22) | IgC1 | N1-P18/47 | ESLTLNVQYEPE-NH$_2$ (SEQ ID NO: 49) |
| N4-P19/19 | AEASVRGLEDQNLW-NH$_2$ (SEQ ID NO: 23) | | N1-P19/48 | PEVTIEGFDGNW-NH$_2$ (SEQ ID NO: 50) |
| N4-P20/20 | LWHIGREGAMLKCL-NH$_2$ (SEQ ID NO: 24) | IgC2 | N1-P20/49 | NWYLQRMDVKLTCK-NH$_2$ (SEQ ID NO: 51) |
| N4-P21/21 | CLSEGQPPPSYNWT-NH$_2$ (SEQ ID NO: 25) | IgC2 | N1-P21/50 | CKADANPPATEYHWT-NH$_2$ (SEQ ID NO: 52) |
| N4-P22/22 | WTRLDGPLPSGVRV-NH$_2$ (SEQ ID NO: 26) | IgC2 | N1-P22/51 | WTTLNGSLPKGVEA-NH$_2$ (SEQ ID NO: 53) |
| N4-P23/23 | RVDGDTLGFPPLTT-NH$_2$ (SEQ ID NO: 27) | IgC2 | N1-P23/52 | EAQNRTLFFKGPINY-NH$_2$ (SEQ ID NO: 54) |
| N4-P24/24 | TTEHSGIYVCHVSN-NH$_2$ (SEQ ID NO: 28) | IgC2 | N1-P24/53 | NYSLAGTYICEATN-NH$_2$ (SEQ ID NO: 55) |
| N4-P25/25 | SNEFSSRDSQVTVD-NH$_2$ (SEQ ID NO: 29) | IgC2 | N1-P25/54 | TNPIGTRSGQVEVN-NH$_2$ (SEQ ID NO: 56) |
| N4-P26/26 | VDVLDPQEDSGKQV-NH$_2$ (SEQ ID NO: 30) | IgC2 | N1-P26/55 | VNITEFPYTPSPPEHGRRA-NH$_2$ (SEQ ID NO: 57) |
| N4-P27/27 | SGKQVDLVSAS-NH$_2$ (SEQ ID NO: 31) | Adjacent to membrane | N1-P27/56 | HGRRAGPVPTA-NH$_2$ (SEQ ID NO: 58) |
| N4-P28/28 | WTRLDGPLPSGVRVDGDT-NH$_2$ (SEQ ID NO: 59) | Intracellular | N1-P28/57 | WTTLNGSLPKGVEAQNRT-NH$_2$ (SEQ ID NO: 61) |
| N4-P29/29 | TGNGIYINGRGHLV-NH$_2$ (SEQ ID NO: 60) | | | |

Cell Adhesion.

Black, clear-bottom 96-well microtiter plates (Corning, Imported Costar, Corning, N.Y.) were coated with recombinant human Nectin-1 extracellular domain (R&D Systems), recombinant human Nectin-4 extracellular domain (R&D Systems), mouse laminin (Invitrogen™), or bovine serum albumin (BSA; Probumin Diagnostic Grade, MilliPore) diluted in PBS. Covered plates were incubated overnight at 37° C. in a humidified incubator. After washing with PBS plus $Ca^{2+}/Mg^{2+}$ containing 2 mg/ml ovalbumin (Sigma-Aldrich), the plates were blocked for 1 hat 37° C. with 1% BSA in PBS without $Ca^{2+}/Mg^{2+}$. Confluent monolayers of NIH:OVCAR5 cells or NIH:OVCAR5-N4-over cells were detached with Accutase, and then filtered through a 40 μm cell strainer (BD Biosciences, San Jose, Calif.) to remove cell aggregates. The single cells were stained with CellTracker Green CMFDA (5-chloromethylfluorescein diacetate; Invitrogen™) according to the manufacturer's protocol. After washing the plate, 30,000 cells were added to each well in 50 μl of RPMI 1640 media containing 2 mg/ml ovalbumin and allowed to adhere for 15-60 min at 37° C. Plates were vigorously washed four times and read in a BioTek Synergy fluorescent microplate reader (BioTek, Winooski, V A). Experiments were conducted in triplicate.

Inhibition of Cell Adhesion with mAbs.

Microtiter plates coated with recombinant Nectin-1 as described above were pre-incubated for 30 min at room temperature with 4 μg/ml of a mAb against Nectin-1 in PBS in triplicate. CMFDA-stained NIH:OVCAR5-N4-over cells were then added to the wells and cell adhesion was quantified as described above. In parallel studies, CMFDA-stained NIH:OVCAR5-N4-over cells were pre-incubated for 30 min at room temperature with 4 μg/ml of mouse IgG or mAbs against Nectin-4, and then the cells and mAbs were added to the 96-well plate. Experiments were conducted in triplicate and repeated four times.

Definition of Nectin Cell Adhesion Domains by Synthetic Peptides.

Microtiter plates coated with recombinant Nectin-1 as described above were pre-incubated for 30 min at room temperature with 150 μg/ml Nectin-4 peptides in PBS in triplicate. CMFDA-stained NIH:OVCAR5-N4-over cells were then added to the wells and cell adhesion was quantified as described above. In parallel studies, CMFDA-stained NIH:OVCAR5-N4-over cells were pre-incubated for 30 min at room temperature with 150 μs/ml Nectin-1 peptides in PBS in triplicate, and then the cells and peptides were added to the 96-well plate. In each experiment, DMSO, which had been used to reconstitute the desiccated peptides, was used at a comparable dilution (1:300) as a control. Experiments were conducted in triplicate. Peptides were screened once and selected peptides were repeated two times.

Spheroid Formation.

Spheroids were formed from the NIH:OVCAR5 cell lines described above using the liquid overlay method [8, 9]. One milliliter of a single cell suspension was seeded at a concentration of 50,000 cells/ml in OptiMEM® media, into 24-well tissue culture plates coated with 0.5% Seakem agarose (in complete RPMI-1640). Plates were incubated at 37° C. in a humidified incubator with 5% $CO_2$. At various time points up to 5 days, the plates were removed from the incubator and the spheroids were photographed with a Nikon CoolPix digital camera mounted on an Olympus CK2 inverted microscope with a 4× objective. The size of the spheroids was determined using the measure tool in Adobe Photoshop. The largest spheroids were quantified (20-90 spheroids/well), in a minimum of 8 wells, for a total of >300 spheroids per cell type.

Cell Migration.

Cells were diluted to a concentration of 300,000-700,000 cells/ml in complete media, and 70 μl was plated into each chamber (0.22 $cm^2$ growth area) of an Ibidi® wound-healing culture-insert (Ibidi®, Verona, Wis.) in triplicate in a 24-well tissue culture plate. Cells were grown overnight at 37° C. in a humidified incubator with 5% $CO_2$ or until the chambers were confluent, prior to removal of the culture insert. Migrating cells were incubated in OptiMEM® containing 10 μM lysophosphatidic acid (LPA), and photographed initially (t=0 h), and then at 2, 4, 6, 8, and 24 h time points with a 4× objective. Image analysis was performed using ImageJ software [59] with the Scratch Assay Analyzer from the MiToBo plug in. Three independent experiments were performed.

Cell Proliferation.

Cell proliferation was determined using the CyQUANT® assay (Invitrogen™) according to the manufacturer's instructions. Briefly, 8000 cells were seeded per well into 96-well microtiter plates in triplicate in complete media and allowed to adhere for 2 h at 37° C. After 2 h, the media was replaced with OptiMEM® reduced serum media and the cells were grown for 24 h and 48 h at 37° C. At each time point, the media was removed, plates were frozen to lyse cells, and the fluorescence was measured in a BioTek Synergy fluorescent microplate reader after adding the CyQUANT® GR dye. Proliferation was calculated as the change in fluorescence relative to the 2 h time point. Experiments were repeated five times.

Results

Generation and Characterization of Cell Lines.

The human ovarian cancer cell line NIH:OVCAR5 was selected for this study in order to understand the potential function of Nectin-4 in ovarian cancer progression. This cell line expresses moderate levels of Nectin-4 on its surface, relative to a dozen other human ovarian cancer cell lines that we had previously characterized [18], and thus, it is ideal for generating cell lines that either have Nectin-4 expression stably knocked down or overexpressed. Nectin-4 knockdown cell lines were created by stable expression of a Nectin-4 targeting shRNA. Cells were transfected with lentivirus containing an shRNA sequence targeting Nectin-4 or control shRNA, and selected with puromycin. Clones of Nectin-4 shRNA expressing cells were screened by RT-PCR (reverse transcription—polymerase chain reaction) for reduced levels of Nectin-4 expression (data not shown), which was verified by flow cytometry (FIG. 1). Three of the selected Nectin-4 shRNA clones (termed VB3, VB9, and VB13) show little to no expression of Nectin-4 [85-100% Nectin-4 knock-down (FIG. 1D-F, red histogram)] relative to the parental cell line (FIG. 1A) or cells that express the control shRNA (FIG. 1C). These cells also express Nectin-1 (FIG. 1, light blue histogram), which has been shown to serve as a binding partner for Nectin-4 [21]. The level of Nectin-1 expression in the engineered NIH:OVCAR5 cells remained similar to that observed in the parental cell line. Conversely, FACS (fluorescence activated cell sorting) was used to select cells that overexpressed full-length Nectin-4 (FIG. 1B) relative to the NIH:OVCAR5 parental cell line in order to facilitate in vitro adhesion assays.

Nectin-4 Expression Increases Cell Adhesion.

Figure 2:
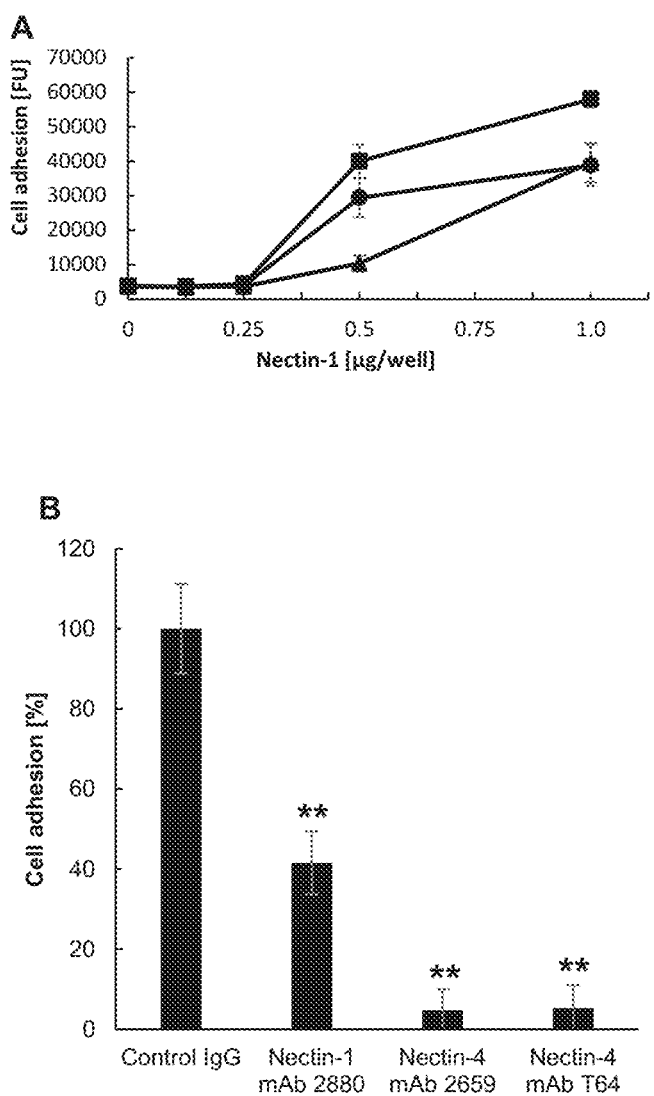
FIGS. 2A-B Adhesion of NIH:OVCAR5-N4-over ovarian cancer cells to Nectin-1. (A) Microtiter plates were coated with increasing amounts of recombinant Nectin-1 extracellular domain. NIH:OVCAR5-N4-over cells were stained with CMFDA and incubated in the plate for 15 min (triangle), 30 min (circle), or 60 min (square). Adherent cells were quantified in a fluorescent plate reader. FU=fluorescent units; Error bars=SD. (B) Microtiter plates were coated with 0.5 µg/well of recombinant Nectin-1 extracellular domain. NIH:OVCAR5-N4-over cells were pre-incubated for 30 min with mouse IgG or mAbs against Nectin-4; and then cells were incubated in the wells for 30 min. In parallel studies, Nectin-1 coated plates were incubated with the mAb against Nectin-1 for 30 min, and then cells were incubated in the wells for 30 min. Cell adhesion was plotted relative to the adhesion observed for mouse IgG; the FU of BSA-coated control wells was subtracted from all samples. Shown is a representative of three independent experiments. Error bars=SD [%]; Student's t-test unpaired **=P<0.01

NIH:OVCAR5 cells that overexpress Nectin-4 (termed NIH:OVCAR5-N4-over) were tested for their ability to adhere to recombinant Nectin-1 and Nectin-4 in an in vitro binding assay. The NIH:OVCAR5-N4-over cells adhered to increasing concentrations of recombinant Nectin-1 extracellular domain in a time-dependent manner (FIG. 2A). However, although Nectin-4 has been reported to bind to itself in a homotypic manner [50], adhesion of the NIH:OVCAR5-N4-over cells to recombinant Nectin-4 was note detectable when cells were incubated for up to 1 h in wells coated with 1 µg of Nectin-4 per well. When NIH:OVCAR5 parental cells were tested in parallel studies, the level of adhesion to Nectin-4 and Nectin-1 was negligible, even when cells were incubated in the wells for up to 1 h at coating concentrations of 1 µg/well (data not shown).

The specificity of cell adhesion to Nectin-1 was examined by use of mAbs against Nectin-1 and Nectin-4 to block the interaction between NIH:OVCAR5-N4-over cells and recombinant Nectin-1. Based on the data from the cell adhesion assay (FIG. 2A), a coating concentration of 0.5 µg/well of Nectin-1 extracellular domain and a length of time for adhesion of 30 min was selected for the inhibition assay, in order to optimize the likelihood of inhibition. mAbs that recognize the extracellular domains of Nectin-1 and Nectin-4 significantly inhibited adhesion of the NIH:OVCAR5-N4-over cells relative to the mouse IgG (immunoglobulin) control mAb (FIG. 2B). The mAbs against Nectin-4 almost completely inhibited cell adhesion to Nectin-1, while the mAb against Nectin-1 inhibited cell adhesion to Nectin-1 by ~60% (FIG. 2B).

Nectin Domains Involved in Cell Adhesion.

Figure 3:
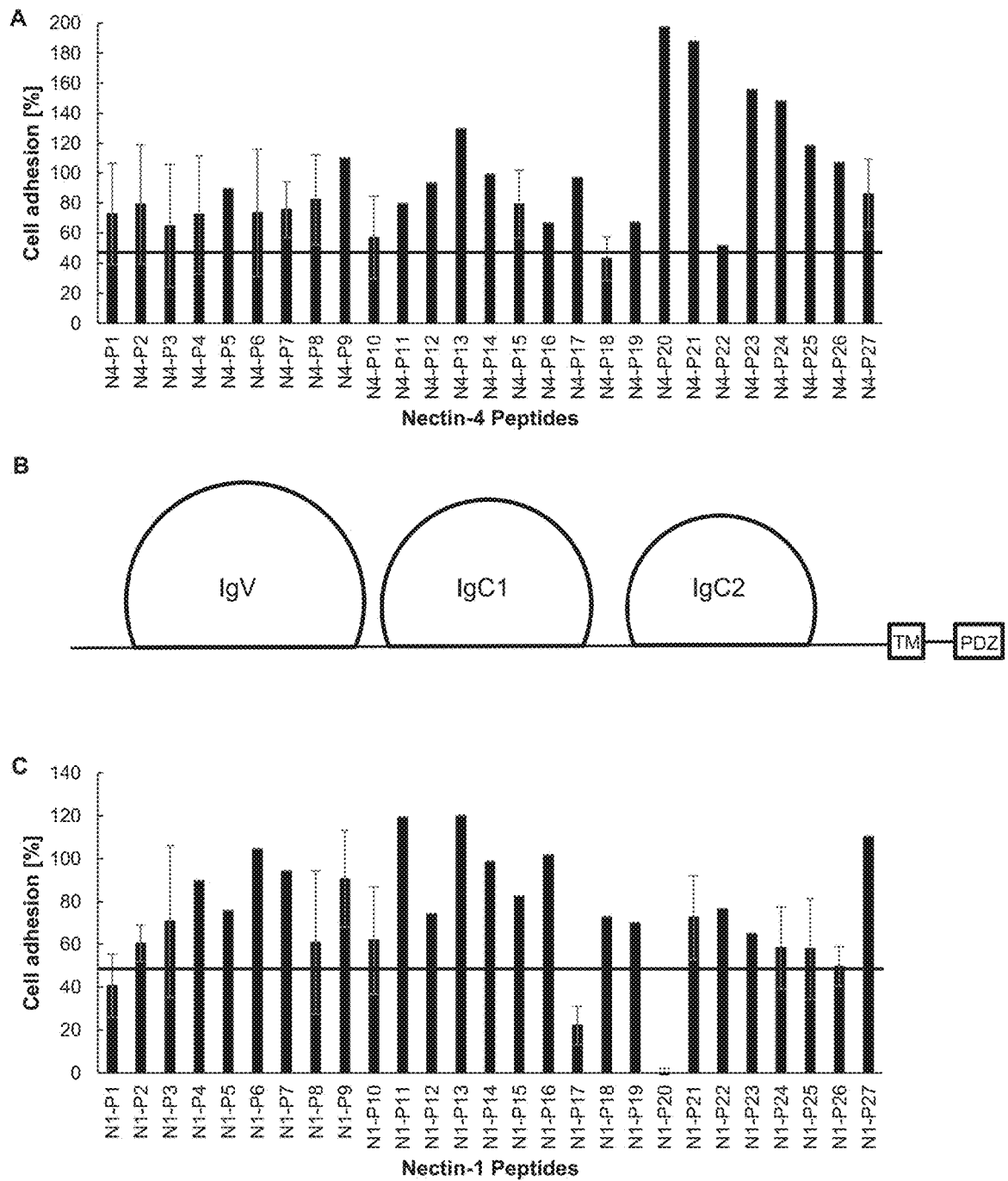
FIGS. 3A-C Identification of binding domains on nectins. Microtiter plates were coated with 0.5 µg/well recombinant Nectin-1 extracellular domain. (A) Triplicate wells were pre-incubated for 30 min with Nectin-4 peptides. CMFDA stained NIH:OVCAR5-N4-over cells were allowed to adhere in the wells for 30 min. (B) A diagrammatic representation of the extracellular domain of Nectin-4 and Nectin-1. TM=Transmembrane Domain, PDZ=Afadin binding domain. (C) CMFDA stained NIH:OVCAR5-N4-over cells were pre-incubated for 30 min with Nectin-1 peptides in triplicate, and then added to the plates for 30 min. Cell adhesion was quantified relative to the adhesion observed with DMSO control; the FU of BSA-coated control wells was subtracted from all samples. The horizontal lines represent 50% adhesion relative to DMSO control. Error bars=SD [%].

Peptides synthesized from the extracellular domains of Nectin-4 and Nectin-1 (Table 1) were screened in the cell adhesion assay to identify smaller regions on the nectins that may alter cell adhesion. A coating concentration of 0.5 µg/well of Nectin-1 and a 30 min incubation period for the NIH:OVCAR5-N4-over cells was used for the inhibition assay. Of the 57 peptides screened, three peptides from Nectin-4 (FIG. 3A; peptides N4-P10, N4-P18, N4-P22, and N4-P29) and four peptides from Nectin-1 (FIG. 3C; peptides N1-P1, N1-P17, N1-P20, and N1-P26) inhibited adhesion of the NIH:OVCAR5-N4-over cells by 50-100% compared to the control. The peptides that most interfered with cell adhesion were derived from sites on the nectins near the IgC domains (FIG. 3B), although one of the adhesion blocking Nectin-1 peptides was the most N-terminal peptide (FIG. 3C). Interestingly, one of the peptides from the IgC2 domain of Nectin-1 (N1-P20) inhibited cell adhesion to a greater extent than the mAb against Nectin-1.

Nectin-4 Expression Increases the Size of Multicellular Spheroids.

Figure 4:
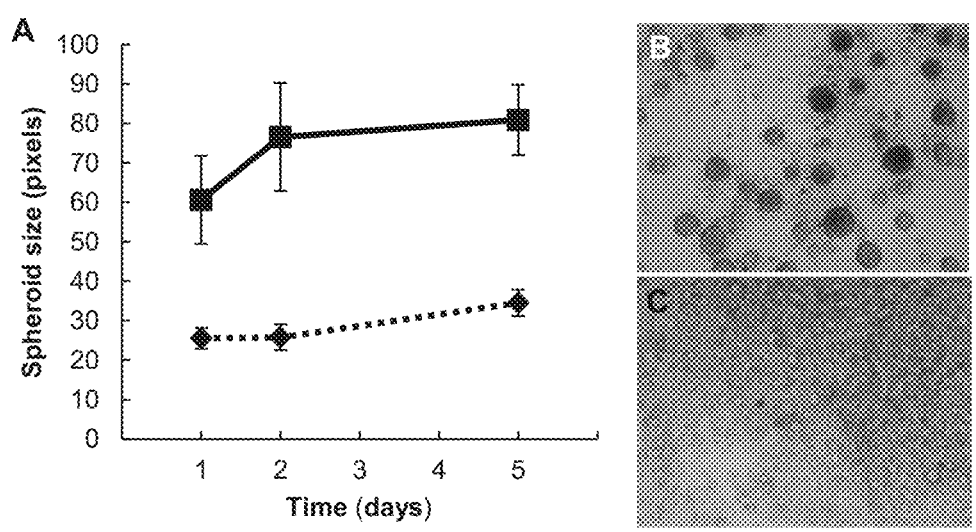
FIGS. 4A-C NIH:OVCAR5 cells that express Nectin-4 make larger spheroids than Nectin-4 knockdown cells. Single cell suspensions of NIH:OVCAR5 cells expressing shRNA targeting Nectin-4 or a control shRNA were plated in agarose-coated tissue culture plates and spheroids were allowed to form for 5 days. (A) Spheroid size was quantified for cells expressing a control shRNA (square with solid line) or cells expressing Nectin-4 shRNA (diamond with dashed line). Error bars=SD. The largest spheroids were quantified (20-90 spheroids/well), in a minimum of 8 wells, for a total of >300 spheroids per cell type. Representative examples of spheroids after 5 days in culture, 40× magnification: (B) NIH:OVCAR5 control shRNA and (C) NIH:OVCAR5-VB3 Nectin-4 knock-down.

The formation of tumor spheroids (free floating, multicellular aggregates) is a unique feature of ovarian cancer progression. To determine whether Nectin-4 expression contributes to spheroid formation, we compared NIH:OVCAR5-VB3 cells (which have Nectin-4 expression abolished by shRNA) to control shRNA cells in a spheroid formation assay (FIG. 4). Single cell suspensions were plated on agarose-coated tissue culture plates, the resulting spheroids were observed over several days, and the size of the spheroids was measured. After 24 h, the NIH:OVCAR5 cells that expressed Nectin-4 (i.e. control shRNA) formed large, compact spheroids (FIG. 4A, solid line) which were significantly larger in size than the spheroids formed by the NIH:OVCAR5-VB3 cells (N4 shRNA, FIG. 4A, dashed line). Over the course of 5 days, the size of the spheroids increased for both cell lines tested; however the Nectin-4 knock-down cells remained significantly smaller than the shRNA controls (FIGS. 4B and 4C).

Figure 5:
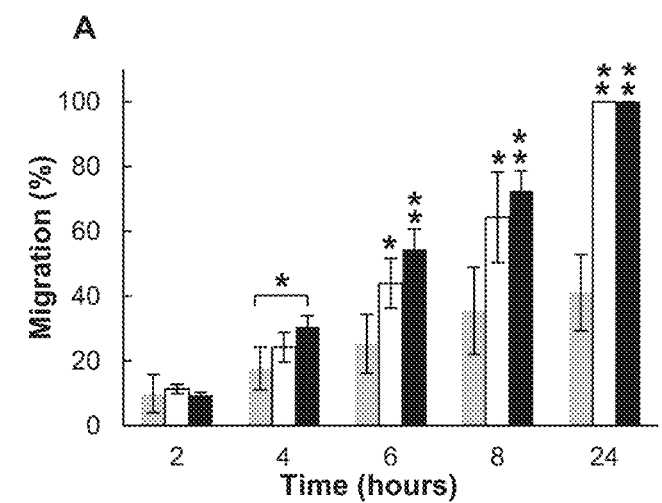
FIGS. 5A-B Nectin-4 expression increases cell migration. Migration of cells was quantified in a wound healing assay and the area of the wound was calculated up to 24 h: (A) NIH:OVCAR5 parental cells (black bars); NIH:OVCAR5 control shRNA cells (white bars); NIH:OVCAR5-VB3 Nectin-4 knockdown cells (gray bars). NIH:OVCAR5 cells expressing Nectin-4 (parental and control shRNA) migrated significantly faster than cells that had Nectin-4 expression knocked-down by shRNA. Shown is a representative assay in which migration of the three Nectin-4 knock-down clones (VB3, VB9, and VB13) was averaged. Error bars=SD. Student's t-test, unpaired: *$P<0.05$, **$P<0.01$. (B) Representative images of wound healing assay at 0 h, 8 h, and 24 h, 40× magnification. Dotted lines indicate the leading edge of the migrating cells.
Figure 5:
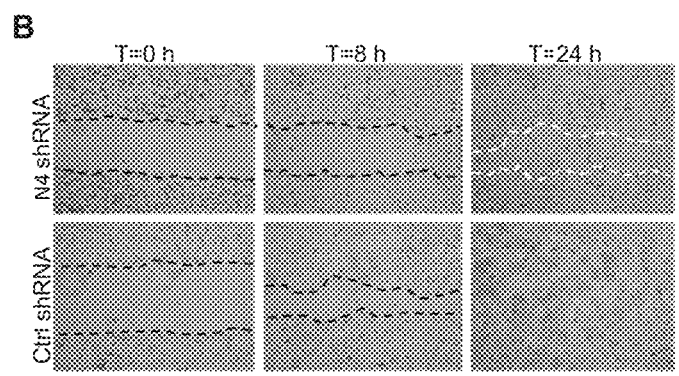

Nectin-4 expression increases cell migration. Due to the link between Nectin-4 and the actin cytoskeleton [21, 51], it was questioned whether Nectin-4 expression could affect ovarian cancer cell migration. To answer this, wound healing assays were performed using NIH:OVCAR5 cells that expressed Nectin-4 (control shRNA and parental cells) or had Nectin-4 expression knocked-down by shRNA, and quantified the area of the wounds at several time-points (FIG. 5). A significant difference in migration between the parental NIH:OVCAR5 cells and the NIH:OVCAR5-Nectin-4 shRNA cells (clones VB3, VB9, and VB13) was seen after 4 h. After 6 h, both the parental NIH:OVCAR5 cells and the control shRNA cells had migrated significantly faster than the NIH:OVCAR5-VB Nectin-4 knock-down cells (FIG. 5A). After 24 h of migration, the NIH:OVCAR5 control shRNA cells had completely closed the area of the wound (FIG. 5B, bottom panels), while the NIH:OVCAR5-VB Nectin-4 knock-down cells had not (FIG. 5B, top panels). While the area of the wound in the Nectin-4 knock-down cells was not closed, some cells migrated into the wound so that the area was sparsely populated (see dotted white lines in FIG. 5B, top panel). No significant difference in migration rate was observed between the three NIH:OVCAR5-Nectin-4 shRNA clones VB3, VB9, and VB13 (data not shown).

Nectin-4 Expression Increases Cell Proliferation.

Figure 6:
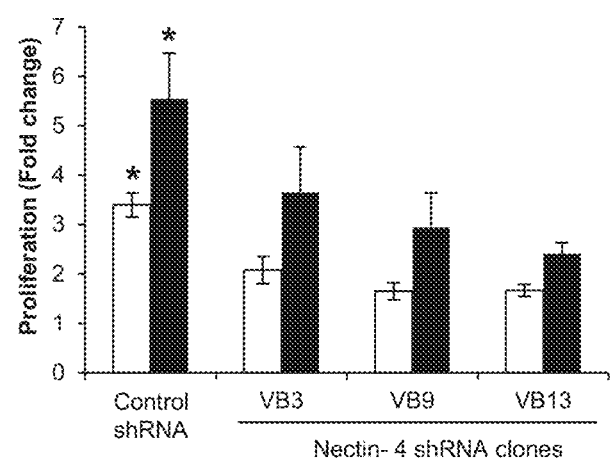
FIG. 6 Nectin-4 expression increases NIH:OVCAR5 cell proliferation. NIH:OVCAR5 control shRNA cells or Nectin-4 shRNA clone (VB3, VB9, and VB13) cells were plated at 8000 cells per well into 96-well microtiter plates and grown in OptiMEM® reduced serum media. The number of cells per well was quantified by the CyQUANT® assay at 24 h (white bar) and 48 h (black bar) after plating, and is represented as the fold change in fluorescence relative to the 2 h timepoint. Values are an average of at 5 independent experiments (error bars=SD). Student's t-test, unpaired: * $p<0.005$.
Figure 7:
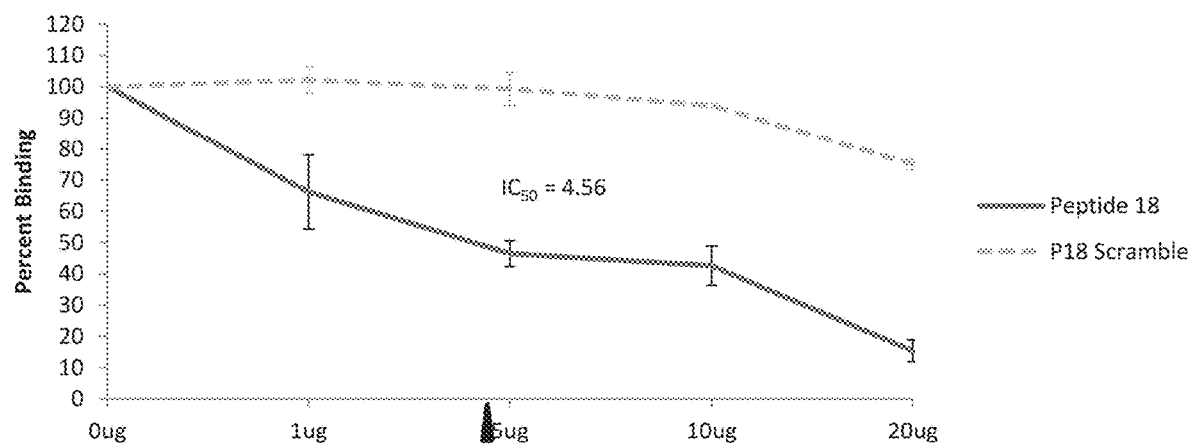
FIG. 7 Provides graphical depiction of data collected in cell binding assays in which scrambled version of some of the peptides are shown; N4 peptide 18 and 18 scramble.
Figure 8:
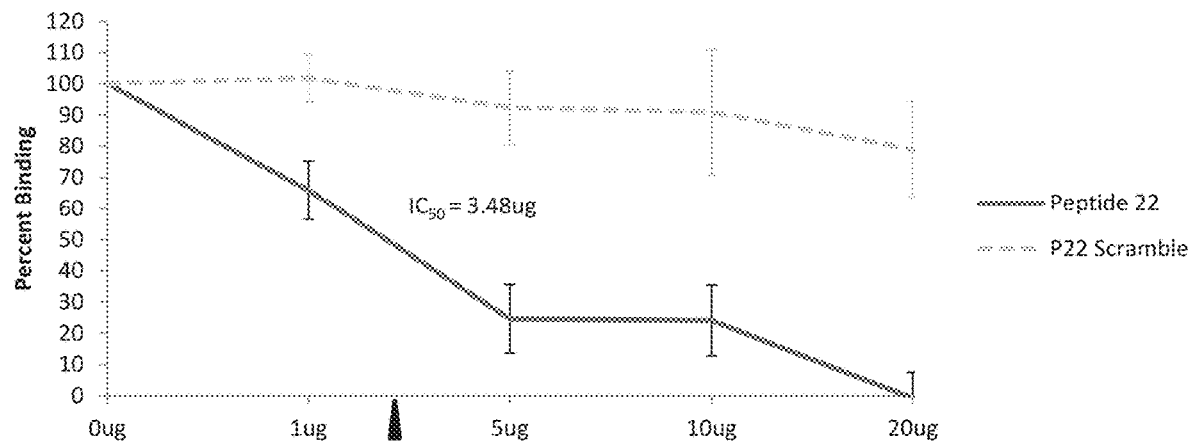
FIG. 8 Provides graphical depiction of data collected in cell binding assays in which scrambled version of some of the peptides are shown; N4 peptide 22 and 22 scramble.
Figure 9:
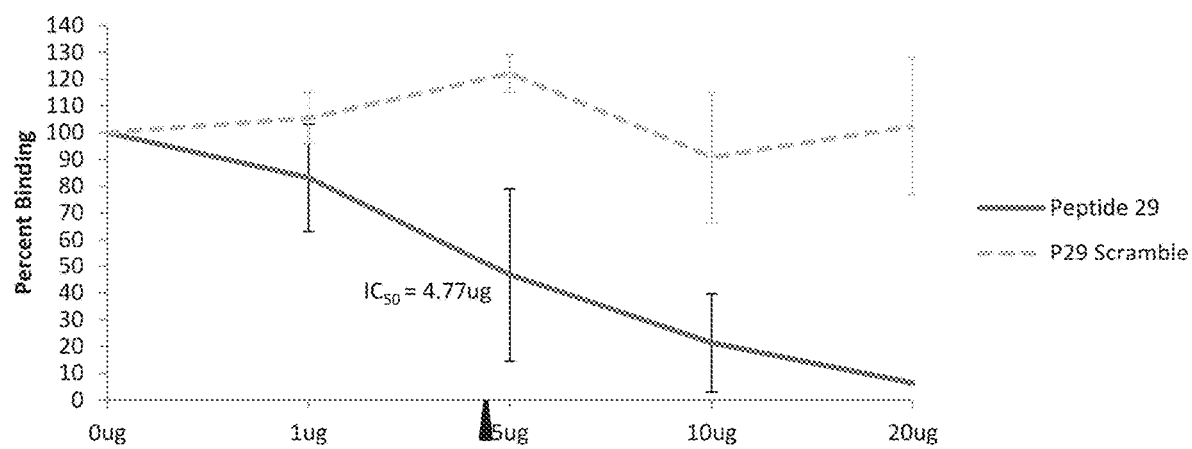
FIG. 9 Provides graphical depiction of data collected in cell binding assays in which scrambled version of some of the peptides are shown: N4 peptide 29 and 29 scramble.
Figure 10:
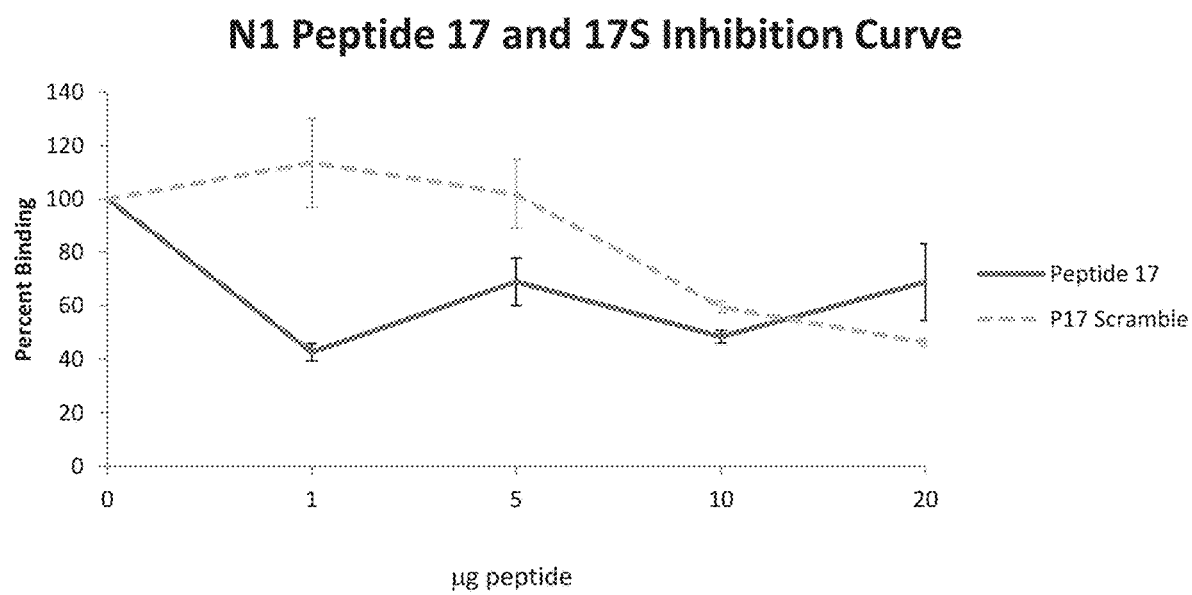
FIG. 10 Provides graphical depiction of data collected in cell binding assays in which scrambled version of some of the peptides are shown; N1 peptide 17 and 17 scramble.
Figure 11:
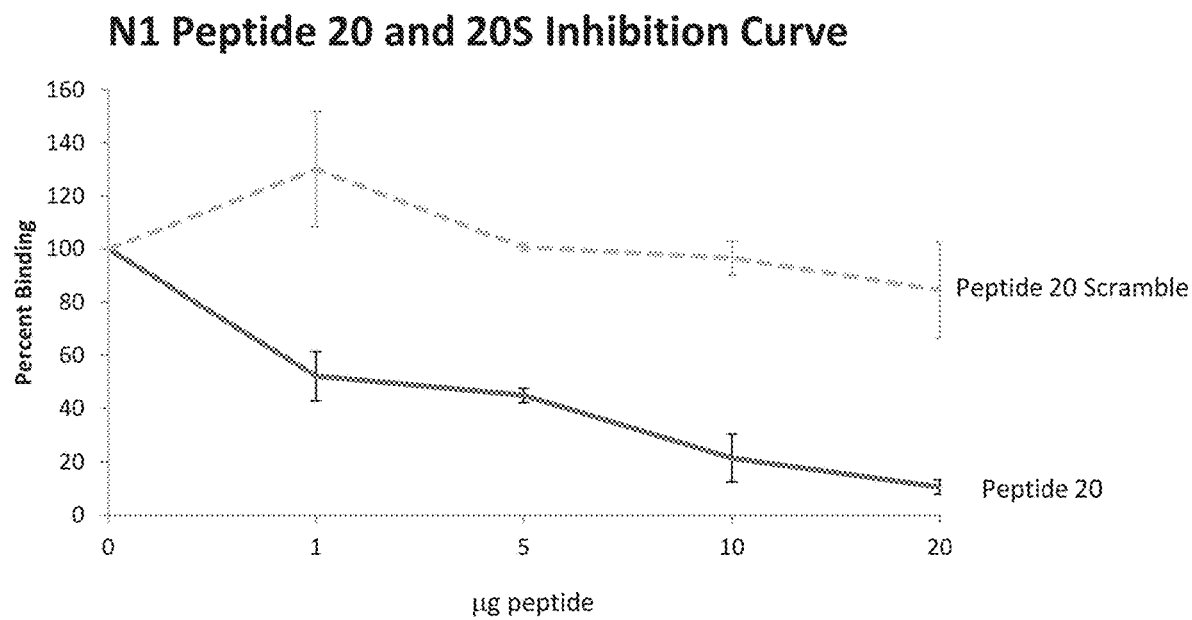
FIG. 11 Provides graphical depiction of data collected in cell binding assays in which scrambled version of some of the peptides are shown; N1 peptide 20 and 20 scramble.

Previous reports have suggested a role for Nectin-4 in cell proliferation [22, 26, 52]. The proliferation rate of NIH:OVCAR5 cells with Nectin-4 knocked-down by shRNA (clones VB3, VB9, and VB13) compared to NIH:OVCAR5 cells that express a control shRNA was measured at 24 h (FIG. 6, white bar) and 48 h (FIG. 6, black bar). The NIH:OVCAR5 cells expressing the control shRNA doubled within approximately 12 h, and increased in number by over 5-fold within 48 h. The three cell lines with Nectin-4 knock-down doubled within approximately 24 h, and had increased by about 3-fold after 48 h (FIG. 6). The rates of proliferation for the three cell lines with Nectin-4 knocked down were not significantly different from each other (FIG. 6). Overall, the cells that expressed Nectin-4 proliferated significantly faster than each of the three lines of NIH:OVCAR5 cells that had Nectin-4 knocked down.

Discussion

The cell adhesion molecule Nectin-4 is normally expressed in early development and is aberrantly overexpressed in some epithelial cancers, including ovarian cancer [17]. In lung cancer, breast cancer, and pancreatic cancer, expression of Nectin-4 or detection of Nectin-4 in serum was associated with tumor progression or poor survival [22-24, 26]. In the experiments presented here, the effect that Nectin-4 expression in ovarian cancer cells has on the various cellular behaviors that underlie metastasis was examined. It was found that in addition to playing a role in cell-cell adhesion, elevated levels of Nectin-4 expression on the surface of ovarian cancer cells increased the size of multicellular aggregates (i.e. spheroids), and increased the rates of cell migration, as well as cell proliferation.

Using an in vitro cell adhesion assay, it was shown that NIH:OVCAR5-N4-over cells adhere to the extracellular domain of Nectin-1 in a time and dose-dependent matter. However, similar adhesion to the extracellular domain of Nectin-4 was not detected. Although homophilic interaction of nectins has previously been reported [40, 53], the Nectin-4 interaction with itself is weaker than its interaction with Nectin-1 [21]. It was shown that mAbs against Nectin-1 and Nectin-4 could significantly inhibit the adhesion of NIH:OVCAR5-N4-over cells to Nectin-1. Furthermore, both of the mAbs against Nectin-4 inhibited cell adhesion more effectively than the mAb against Nectin-1. It is possible that this is due to the different epitopes recognized by the mAbs. Fabre et al. [39] have reported that the most distal domains of the nectins (the IgV domains) are sufficient to mediate binding between Nectin-4 and Nectin-1, while the membrane proximal IgC domains affect binding affinity. Reymond et al. [21] also reported that antibodies against the IgV domain of Nectin-1 disrupt the Nectin-4-Nectin-1 interaction, suggesting that the epitope recognized by mAb 2880 against Nectin-1 (used in this study) may reside in another region of the Nectin-1 extracellular domain. The results provided herein corroborate these findings since it was shown that mAb T64, which recognizes the IgV domain of Nectin-4 [39], caused almost complete inhibition of cell adhesion to Nectin-1. The epitopes recognized by Nectin-1 mAb 2880 and Nectin-4 mAb 2659 have not been identified. Peptides synthesized from the extracellular domains of Nectin-1 and Nectin-4 (Table 1) were screened for their ability to inhibit cell adhesion to the recombinant Nectin-1 extracellular domain. Several peptides from both Nectin-1 and Nectin-4 inhibited cell adhesion of NIH:OVCAR5-N4-over cells to Nectin-1 by at least 50%, while one Nectin-1 peptide showed complete inhibition (N1-P20). Interestingly, the peptides that inhibited cell adhesion to Nectin-1 to the greatest extent were in the IgC domains, in contrast to the adhesion blocking mAbs against Nectin-4 which recognize the IgV domain. Perhaps, due to the small size of the peptides (14-18 amino acids), cell adhesion is inhibited by the peptides binding the IgC domain and causing a conformational change, rather than physically blocking the protein-protein interaction. Remarkably, it was also observed that several peptides from the IgC2 domain of Nectin-4 promoted cell adhesion to Nectin-1, possibly by "bridging" interactions between the Nectin-1 on the plate and Nectin-1 or Nectin-4 on the cell surface. Whether the Nectin-1 or Nectin-4 peptides can inhibit (or promote) other Nectin-4 functions, such as spheroid formation, migration, or proliferation, will be the focus of future studies.

Ovarian cancer is unique in that tumor cells commonly grow within the peritoneal cavity as free floating multicellular aggregates (spheroids) in the ascites fluid. It was shown that NIH:OVCAR5 cells expressing Nectin-4 formed significantly larger spheroids than the Nectin-4 knockdown cells. Spheroids formed by both cell types appeared tightly aggregated, in contrast to previous results with the cell adhesion molecule claudin-4, where cells depleted of claudin-4 formed spheroids more slowly and the spheroids formed had increased paracellular permeability [54]. To determine whether the difference in spheroid size between Nectin-4 expressing and Nectin-4 knockdown cells could be related to the difference in their rates of cell proliferation, cells were pretreated with mitomycin C, a chemical that inhibits cell proliferation by DNA alkylation [55]. No difference was observed in the aggregation of the NIH:OVCAR5-VB3 cells with Nectin-4 knocked down by shRNA when mitomycin C was present. However, the spheroids formed by the shRNA control NIH:OVCAR5 cells treated with mitomycin C were smaller than the untreated control cells after 24 h, suggesting that in the absence of mitomycin C the cells within the spheroids are able to proliferate (data not shown). Similarly, a recent study by Pavlova et al [49] showed that Nectin-4 expression in breast cancer cells promotes anchorage independent cell survival and proliferation through cell-cell adhesion.

Furthermore, it was found that NIH:OVCAR5 cells expressing Nectin-4 were able to migrate faster than the Nectin-4 knock-down cells in wound healing assays. NIH:OVCAR5 cells expressing a control shRNA completely closed the wound within 24 h. In contrast, the Nectin-4 knockdown cells did not completely close the wounds during the 24 h incubation period; instead, cells migrated randomly into the wound area. This observation suggests that the Nectin-4 knock-down cells lack directional migration or that the cells expressing Nectin-4 may adhere to one another and thus migrate en masse instead of migrating as single cells [56, 57]. Takano et al [26] have shown that COS-7 cells and NIH-3T3 cells that have been genetically engineered to express Nectin-4 have increased migration/invasive potential, as well as increased lamellipodia formation and activated Rac1 signaling.

The findings demonstrate that Nectin-4 expression in ovarian cancer can contribute to tumor progression. In the ovarian cancer cell line NIH:OVCAR5, cells that express Nectin-4 proliferated significantly faster than cells that had Nectin-4 expression knocked down by shRNA. A similar proliferative advantage for Nectin-4 expressing cells was recently shown in pancreatic cancer [22] and in lung cancer [26]. In a mouse model, lung cancer cells that express Nectin-4 injected into the flanks of mice showed increased tumor proliferation compared to lung cancer cells without endogenous Nectin-4 expression [26].

In this study, it was shown that the cell adhesion molecule Nectin-4 promotes cell adhesion and migration, as well as cell proliferation and the formation of multicellular spheroids. Taken together, these data suggest that Nectin-4 may play a role in local ovarian cancer progression by promoting tumor proliferation, migration, and invasion into the mesothelial cell lining of the peritoneum. However, a new study has demonstrated that ovarian cancer may also spread via hematogenous metastasis [3]. In pancreatic cancer, Nectin-4 expression detected by immunohistochemistry correlated with vascular endothelial growth factor expression by quantitative RT-PCR. High Nectin-4 expression was also associated with increased microvessel density, suggesting a role for Nectin-4 in angiogenesis [22] and potentially in hematogenous metastasis as well.

The expression of Nectin-4 on the surface of ovarian cancer tumors [17-19] suggests that Nectin-4 is a valid target for therapy. The results presented herein showed that ovarian cancer cells that express Nectin-4 can adhere, form spheroids, migrate and proliferate to a greater extent than cells lacking Nectin-4. The in vitro data showed that a mAb against the IgV domain of Nectin-4 almost completely blocked ovarian cancer cell adhesion to Nectin-1. Pavlova et al. [49] used this same mAb in a mouse xenograft model of breast cancer and observed disruption of tumor cell adhesion and reduced tumor growth in vivo compared to tumors treated with control IgG [49]. In contrast, the mAb which Takano et al. generated against the extracellular domain of Nectin-4 [26] was not tested for its ability to block cell adhesion. In their studies, treatment with their mAb against Nectin-4 did not reduce tumor size in lung cancer xenografts [26]; indicating that blocking Nectin-4 cell adhesion may be an important component of therapeutic efficacy for a mAb in this setting. Future studies will be required to determine if treatment with adhesion-blocking antibodies or antibody-conjugate therapies could be used for the treatment of ovarian cancer and other Nectin-4 expressing epithelial cancers.

BIBLIOGRAPHY

1. Siegel R L, Miller K D and Jemal A. Cancer statistics, 2015. CA: a cancer journal for clinicians. 2015; 65(1):5-29.

2. Romero I and Bast R C, Jr. Minireview: human ovarian cancer: biology, current management, and paths to personalizing therapy. Endocrinology. 2012; 153(4):1593-1602.
3. Pradeep S, Kim S W, Wu S Y, Nishimura M, Chaluvally-Raghavan P, Miyake T, Pecot C V, Kim S J, Choi H J, Bischoff F Z, Mayer J A, Huang L, Nick A M, Hall C S, Rodriguez-Aguayo C, Zand B, et al. Hematogenous metastasis of ovarian cancer: rethinking mode of spread. Cancer cell. 2014; 26(1):77-91.
4. Perets R and Drapkin R. It's Totally Tubular . . . Riding The New Wave of Ovarian Cancer Research. Cancer research. 2016; 76(1):10-17.
5. Yoshida Y, Kurokawa T, Nishikawa Y, Orisa M, Kleinman H K and Kotsuji F. Laminin-1-derived scrambled peptide AG73T disaggregates laminin-1-induced ovarian cancer cell spheroids and improves the efficacy of cisplatin. International journal of oncology. 2008; 32(3):673-681.
6. Desoize B and Jardillier J. Multicellular resistance: a paradigm for clinical resistance? Critical reviews in oncology/hematology. 2000; 36(2-3):193-207.
7. Burleson K M, Casey R C, Skubitz K M, Pambuccian S E, Oegema T R, Jr. and Skubitz A P. Ovarian carcinoma ascites spheroids adhere to extracellular matrix components and mesothelial cell monolayers. Gynecologic oncology. 2004; 93(1):170-181.
8. Burleson K M, Hansen L K and Skubitz A P. Ovarian carcinoma spheroids disaggregate on type I collagen and invade live human mesothelial cell monolayers. Clinical & experimental metastasis. 2004; 21(8):685-697.
9. Casey R C, Burleson K M, Skubitz K M, Pambuccian S E, Oegema T R, Jr., Ruff L E and Skubitz A P. Beta 1-integrins regulate the formation and adhesion of ovarian carcinoma multicellular spheroids. The American journal of pathology. 2001; 159(6):2071-2080.
10. Kenny H A, Chiang C Y, White E A, Schryver E M, Habis M, Romero I L, Ladanyi A, Penicka C V, George J, Matlin K, Montag A, Wroblewski K, Yamada S D, Mazar A P, Bowtell D and Lengyel E. Mesothelial cells promote early ovarian cancer metastasis through fibronectin secretion. The Journal of clinical investigation. 2014; 124(10): 4614-4628.
11. Lengyel E, Burdette J E, Kenny H A, Matei D, Pilrose J, Haluska P, Nephew K P, Hales D B and Stack M S. Epithelial ovarian cancer experimental models. Oncogene. 2014; 33(28):3619-3633.
12. Burleson K M, Boente M P, Pambuccian S E and Skubitz A P. Disaggregation and invasion of ovarian carcinoma ascites spheroids. Journal of translational medicine. 2006; 4:6.
13. Davidowitz R A, Selfors L M, Iwanicki M P, Elias K M, Karst A, Piao H, Ince T A, Drage M G, Dering J, Konecny G E, Matulonis U, Mills G B, Slamon D J, Drapkin R and Brugge J S. Mesenchymal gene program-expressing ovarian cancer spheroids exhibit enhanced mesothelial clearance. The Journal of clinical investigation. 2014; 124(6): 2611-2625.
14. Kenny H A, Dogan S, Zillhardt M, A K M, Yamada S D, Krausz T and Lengyel E. Organotypic models of metastasis: A three-dimensional culture mimicking the human peritoneum and omentum for the study of the early steps of ovarian cancer metastasis. Cancer treatment and research. 2009; 149:335-351.
15. Peart T, Ramos Valdes Y, Correa R J, Fazio E, Bertrand M, McGee J, Prefontaine M, Sugimoto A, DiMattia G E and Shepherd T G. Intact LKB1 activity is required for survival of dormant ovarian cancer spheroids. Oncotarget. 2015; 6(26):22424-22438.
16. Stadlmann S, Feichtinger H, Mikuz G, Marth C, Zeimet A G, Herold M, Knabbe C and Offner F A. Interactions of human peritoneal mesothelial cells with serous ovarian cancer cell spheroids—evidence for a mechanical and paracrine barrier function of the peritoneal mesothelium. International journal of gynecological cancer: official journal of the International Gynecological Cancer Society. 2014; 24(2):192-200.
17. Hibbs K, Skubitz K M, Pambuccian S E, Casey R C, Burleson K M, Oegema T R, Jr., Thiele J J, Grindle S M, Bliss R L and Skubitz A P. Differential gene expression in ovarian carcinoma: identification of potential biomarkers. The American journal of pathology. 2004; 165(2):397-414.
18. Derycke M S, Pambuccian S E, Gilks C B, Kalloger S E, Ghidouche A, Lopez M, Bliss R L, Geller M A, Argenta P A, Harrington K M and Skubitz A P. Nectin 4 overexpression in ovarian cancer tissues and serum: potential role as a serum biomarker. American journal of clinical pathology. 2010; 134(5):835-845.
19. Nabih E S, Abdel Motaleb F I and Salama F A. The diagnostic efficacy of nectin 4 expression in ovarian cancer patients. Biomarkers: biochemical indicators of exposure, response, and susceptibility to chemicals. 2014; 19(6):498-504.
20. Brancati F, Fortugno P, Bottillo I, Lopez M, Josselin E, Boudghene-Stambouli O, Agolini E, Bernardini L, Bellacchio E, Iannicelli M, Rossi A, Dib-Lachachi A, Stuppia L, Palka G, Mundlos S, Stricker S, et al. Mutations in PVRL4, encoding cell adhesion molecule nectin-4, cause ectodermal dysplasia-syndactyly syndrome. American journal of human genetics. 2010; 87(2):265-273.
21. Reymond N, Fabre S, Lecocq E, Adelaide J, Dubreuil P and Lopez M. Nectin4/PRR4, a new afadin-associated member of the nectin family that trans-interacts with nectin1/PRR1 through V domain interaction. The Journal of biological chemistry. 2001; 276(46):43205-43215.
22. Nishiwada S, Sho M, Yasuda S, Shimada K, Yamato I, Akahori T, Kinoshita S, Nagai M, Konishi N and Nakajima Y. Nectin-4 expression contributes to tumor proliferation, angiogenesis and patient prognosis in human pancreatic cancer. Journal of experimental & clinical cancer research: CR. 2015; 34:30.
23. Lattanzio R, Ghasemi R, Brancati F, Sorda R L, Tinari N, Perracchio L, Iacobelli S, Mottolese M, Natali P G and Piantelli M. Membranous Nectin-4 expression is a risk factor for distant relapse of T1-T2, N0 luminal-A early breast cancer. Oncogenesis. 2014; 3:e118.
24. Fabre-Lafay S, Monville F, Garrido-Urbani S, Berruyer-Pouyet C, Ginestier C, Reymond N, Finetti P, Sauvan R, Adelaide J, Geneix J, Lecocq E, Popovici C, Dubreuil P, Viens P, Goncalves A, Charafe-Jauffret E, et al. Nectin-4 is a new histological and serological tumor associated marker for breast cancer. BMC cancer. 2007; 7:73.
25. Fabre-Lafay S, Garrido-Urbani S, Reymond N, Goncalves A, Dubreuil P and Lopez M. Nectin-4, a new serological breast cancer marker, is a substrate for tumor necrosis factor-alpha-converting enzyme (TACE)/ADAM-17. The Journal of biological chemistry. 2005; 280(20):19543-19550.
26. Takano A, Ishikawa N, Nishino R, Masuda K, Yasui W, Inai K, Nishimura H, Ito H, Nakayama H, Miyagi Y, Tsuchiya E, Kohno N, Nakamura Y and Daigo Y. Identification of nectin-4 oncoprotein as a diagnostic and therapeutic target for lung cancer. Cancer research. 2009; 69(16):6694-6703.
27. Agensys, Inc. (2014). A Phase 1 Study of the Safety and Pharmacokinetics of Escalating Doses of ASG-22CE Given as Monotherapy in Subjects With Metastatic Urothelial Cancer and Other Malignant Solid Tumors That Express Nectin-4. In: ClinicalTrials.gov. Bethesda (Md.): National Library of Medicine (US). Available from: https://clinicaltrials.gov/ct2/show/NCT02091999 NLM Identifier: NCT02091999.
28. Takai Y and Nakanishi H. Nectin and afadin: novel organizers of intercellular junctions. Journal of cell science. 2003; 116(Pt 1):17-27.
29. Kurita S, Ogita H and Takai Y. Cooperative role of nectin-nectin and nectin-afadin interactions in formation of nectin-based cell-cell adhesion. The Journal of biological chemistry. 2011; 286(42):36297-36303.
30. Yamada A, Fujita N, Sato T, Okamoto R, Ooshio T, Hirota T, Morimoto K, Irie K and Takai Y. Requirement of nectin, but not cadherin, for formation of claudin-based tight junctions in annexin II-knockdown MDCK cells. Oncogene. 2006; 25(37):5085-5102.
31. Fukuhara A, Irie K, Yamada A, Katata T, Honda T, Shimizu K, Nakanishi H and Takai Y. Role of nectin in organization of tight junctions in epithelial cells. Genes to cells: devoted to molecular & cellular mechanisms. 2002; 7(10):1059-1072.
32. Honda T, Shimizu K, Fukuhara A, Irie K and Takai Y. Regulation by nectin of the velocity of the formation of adherens junctions and tight junctions. Biochemical and biophysical research communications. 2003; 306(1):104-109.
33. Takahashi K, Nakanishi H, Miyahara M, Mandai K, Satoh K, Satoh A, Nishioka H, Aoki J, Nomoto A, Mizoguchi A and Takai Y. Nectin/PRR: an immunoglobulin-like cell adhesion molecule recruited to cadherin-based adherens junctions through interaction with Afadin, a PDZ domain-containing protein. The Journal of cell biology. 1999; 145(3):539-549.
34. Sakisaka T and Takai Y. Biology and pathology of nectins and nectin-like molecules. Current opinion in cell biology. 2004; 16(5):513-521.
35. Yasumi M, Shimizu K, Honda T, Takeuchi M and Takai Y. Role of each immunoglobulin-like loop of nectin for its cell-cell adhesion activity. Biochemical and biophysical research communications. 2003; 302(1):61-66.
36. Kim D Y, Ingano L A and Kovacs D M. Nectin-1alpha, an immunoglobulin-like receptor involved in the formation of synapses, is a substrate for presenilin/gamma-secretase-like cleavage. The Journal of biological chemistry. 2002; 277(51):49976-49981.
37. Kim J, Lilliehook C, Dudak A, Prox J, Saftig P, Federoff H J and Lim S T. Activity-dependent alpha-cleavage of nectin-1 is mediated by a disintegrin and metalloprotease 10 (ADAM10). The Journal of biological chemistry. 2010; 285(30):22919-22926.
38. Lim S T, Chang A, Giuliano R E and Federoff H J. Ectodomain shedding of nectin-1 regulates the maintenance of dendritic spine density. Journal of neurochemistry. 2012; 120(5):741-751.
39. Fabre S, Reymond N, Cocchi F, Menotti L, Dubreuil P, Campadelli-Fiume G and Lopez M. Prominent role of the Ig-like V domain in trans-interactions of nectins. Nectin3 and nectin 4 bind to the predicted C-C'-C"-D beta-strands of the nectin1 V domain. The Journal of biological chemistry. 2002; 277(30):27006-27013.
40. Irie K, Shimizu K, Sakisaka T, Ikeda W and Takai Y. Roles and modes of action of nectins in cell-cell adhesion. Seminars in cell & developmental biology. 2004; 15(6): 643-656.
41. Amano H, Ikeda W, Kawano S, Kajita M, Tamaru Y, Inoue N, Minami Y, Yamada A and Takai Y. Interaction and localization of Necl-5 and PDGF receptor beta at the leading edges of moving NIH3T3 cells: Implications for directional cell movement. Genes to cells: devoted to molecular & cellular mechanisms. 2008; 13(3):269-284.
42. Bojesen K B, Clausen O, Rohde K, Christensen C, Zhang L, Li S, Kohler L, Nielbo S, Nielsen J, Gjorlund M D, Poulsen F M, Bock E and Berezin V. Nectin-1 binds and signals through the fibroblast growth factor receptor. The Journal of biological chemistry. 2012; 287(44): 37420-37433.
43. Kajita M, Ikeda W, Tamaru Y and Takai Y. Regulation of platelet-derived growth factor-induced Ras signaling by poliovirus receptor Necl-5 and negative growth regulator Sprouty2. Genes to cells: devoted to molecular & cellular mechanisms. 2007; 12(3):345-357.
44. Kanzaki N, Ogita H, Komura H, Ozaki M, Sakamoto Y, Majima T, Ijuin T, Takenawa T and Takai Y. Involvement of the nectin-afadin complex in PDGF-induced cell survival. Journal of cell science. 2008; 121(Pt 12):2008-2017.
45. Kinugasa M, Amano H, Satomi-Kobayashi S, Nakayama K, Miyata M, Kubo Y, Nagamatsu Y, Kurogane Y, Kureha F, Yamana S, Hirata K, Miyoshi J, Takai Y and Rikitake Y. Necl-5/poliovirus receptor interacts with VEGFR2 and regulates VEGF-induced angiogenesis. Circulation research. 2012; 110(5):716-726.
46. Minami A, Mizutani K, Waseda M, Kajita M, Miyata M, Ikeda W and Takai Y. Necl-5/PVR enhances PDGF-induced attraction of growing microtubules to the plasma membrane of the leading edge of moving NIH3T3 cells. Genes to cells: devoted to molecular & cellular mechanisms. 2010; 15(11):1123-1135.
47. Ogita H and Takai Y. Cross-talk among integrin, cadherin, and growth factor receptor: roles of nectin and nectin-like molecule. International review of cytology. 2008; 265:1-54.
48. Sakisaka T, Ikeda W, Ogita H, Fujita N and Takai Y. The roles of nectins in cell adhesions: cooperation with other cell adhesion molecules and growth factor receptors. Current opinion in cell biology. 2007; 19(5):593-602.
49. Pavlova N N, Pallasch C, Elia A E, Braun O, Westbrook T F, Hemann M and Elledge S J. A role for PVRL4-driven cell-cell interactions in tumorigenesis. eLife. 2013; 2:e00358.
50. Takai Y, Irie K, Shimizu K, Sakisaka T and Ikeda W. Nectins and nectin-like molecules: roles in cell adhesion, migration, and polarization. Cancer science. 2003; 94(8): 655-667.
51. Nakanishi H and Takai Y. Roles of nectins in cell adhesion, migration and polarization. Biological chemistry. 2004; 385(10):885-892.
52. Ogita H, Ikeda W and Takai Y. Roles of cell adhesion molecules nectin and nectin-like molecule-5 in the regulation of cell movement and proliferation. Journal of microscopy. 2008; 231(3):455-465.
53. Satoh-Horikawa K, Nakanishi H, Takahashi K, Miyahara M, Nishimura M, Tachibana K, Mizoguchi A and Takai Y. Nectin-3, a new member of immunoglobulin-like cell adhesion molecules that shows homophilic and heterophilic cell-cell adhesion activities. The Journal of biological chemistry. 2000; 275(14):10291-10299.

54. Boylan K L, Misemer B, Derycke M S, Andersen J D, Harrington K M, Kalloger S E, Gilks C B, Pambuccian S E and Skubitz A P. Claudin 4 Is Differentially Expressed between Ovarian Cancer Subtypes and Plays a Role in Spheroid Formation. International journal of molecular sciences. 2011; 12(2):1334-1358.
55. Tomasz M, Lipman R, Chowdary D, Pawlak J, Verdine G L and Nakanishi K. Isolation and structure of a covalent cross-link adduct between mitomycin C and DNA. Science. 1987; 235(4793):1204-1208.
56. Yin B, Li K H, An T, Chen T and Peng X Z. Nectin-like molecule 1 inhibits the migration and invasion of U251 glioma cells by regulating the expression of an extracellular matrix protein osteopontin. Chinese medical sciences journal=Chung-kuo i hsueh k'o hsueh tsa chih/ Chinese Academy of Medical Sciences. 2010; 25(2):100-104.
57. Wang C, Chowdhury S, Driscoll M, Parent C A, Gupta S K and Losert W. The interplay of cell-cell and cell-substrate adhesion in collective cell migration. Journal of the Royal Society, Interface/the Royal Society. 2014; 11(100):20140684.
58. Hamilton T C, Young R C and Ozols R F. Experimental model systems of ovarian cancer: applications to the design and evaluation of new treatment approaches. Seminars in oncology. 1984; 11(3):285-298.
59. Schneider C A, Rasband W S and Eliceiri K W. NIH Image to ImageJ: 25 years of image analysis. Nature methods. 2012; 9(7):671-675.

Example II

Materials and Methods

Effect of Peptides on Antibody Binding to Cells as Determined by Flow Cytometry:

Briefly, NIH:OVCAR-5 cells that natively express a moderate amount of nectin 4 protein were incubated for 30 minutes in 150 µg/mL of soluble peptide in DMSO. After incubation, the cells were washed, and then triple antibody stained using mouse anti-nectin 4 (or IgG control) primary antibody, biotinylated goat anti-mouse secondary antibody, and streptavidin APC tertiary antibody. Finally, utilizing the University of Minnesota flow core's Accuri C6 flow cytometer, the relative antibody binding affinity for control and peptide-treated samples was quantitated and compared. Data was collected for each of the 57 peptides generated.

Inhibition of Cell Adhesion with Scrambled Version of Peptides:

Clear-bottom 96 well plates were coated in recombinant human nectin 1 extracellular domain at various concentrations and treated with bovine serum albumin, synthetic peptides, or antibodies. Cells overexpressing nectin-4 and treated with CellTracker Green dye were then introduced to the wells, allowed to bind for a short period, and then rinsed off with PBS. A fluorescent plate reader was used to determine the strength of the signal from each well to determine whether or not binding was inhibited by peptides or antibodies.

Results:

Effect of nectin peptides on the ability of a monoclonal antibody against Nectin-4 to bind to ovarian cancer cells, as determined by flow cytometry. Data is summarized in the tables below and in FIG. 12.

Effect of Nectin-4 Peptides on the Ability of a Monoclonal Antibody Against Nectin-4 to Bind to Ovarian Cancer Cells, as Determined by Flow Cytometry.

| Run One Peptide Number | N4 MFI | IgG MFI | N4 MFI/ IgG MFI | [(Sn − Si)/ (Cn − Cl)] * 100 |
|---|---|---|---|---|
| Control 1 | 15,015 | 1,670 | 8.99 | 100.00 |
| Peptide 1 | 2,085 | 1,529 | 1.36 | 4.17 |
| Peptide 2 | 11,895 | 2,458 | 4.84 | 70.72 |
| Peptide 3 | 6,987 | 2,044 | 3.42 | 37.04 |
| Peptide 4 | 8,687 | 2,199 | 3.95 | 48.62 |
| Peptide 5 | 11,668 | 1,711 | 6.82 | 74.61 |
| Peptide 6 | 12,682 | 1,622 | 7.82 | 82.88 |
| Peptide 7 | 18,342 | 1,255 | 14.62 | 128.04 |
| Peptide 8 | 20,015 | 1,670 | 11.99 | 137.47 |
| Peptide 9 | 8,578 | 1,886 | 4.55 | 50.15 |
| Peptide 10 | 4,119 | 2,452 | 1.68 | 12.49 |
| Peptide 11 | 15,211 | 2,268 | 6.71 | 96.99 |
| Peptide 12 | 11,052 | 2,827 | 3.91 | 61.63 |
| Peptide 13 | 15,623 | 3,720 | 4.20 | 89.19 |
| Peptide 14 | 13,217 | 3,125 | 4.23 | 75.62 |
| Peptide 15 | 7,980 | 2,158 | 3.70 | 43.63 |
| Peptide 16 | 12,161 | 2,432 | 5.00 | 72.90 |
| Peptide 17 | 20,511 | 8,686 | 2.36 | 88.61 |
| Peptide 19 | 7,278 | 2,254 | 3.23 | 37.65 |
| Peptide 20 | 17,636 | 1,890 | 9.33 | 117.99 |

The data demonstrate that peptides 1, 3, 4, 9, 10, 15 and 19 provide a reduction in nectin-4 antibody binding compared to untreated control cells. Further peptides, 7, 8 and 20 demonstrate an increased binding of nectin-4 antibody versus control.

| Run Two Peptide Number | N4 MFI | IgG MFI | N4 MFI/ IgG MFI | [(Sn − Si)/ (Cn − Cl)] * 100 |
|---|---|---|---|---|
| Control 2 | 49,491 | 5,233 | 9.46 | 100.00 |
| Peptide 21 | 34,351 | 3,989 | 8.61 | 68.60 |
| Peptide 22 | 70,336 | 7,160 | 9.82 | 142.74 |
| Peptide 23 | 18,902 | 3,342 | 5.66 | 35.16 |
| Peptide 24 | 33,353 | 3,808 | 8.76 | 66.76 |
| Peptide 25 | 7,756 | 3,584 | 2.16 | 9.43 |
| Peptide 26 | 35,299 | 3,956 | 8.92 | 70.82 |
| Peptide 27 | 22,824 | 4,099 | 5.57 | 42.31 |
| Peptide 28 | 41,302 | 3,815 | 10.83 | 84.70 |
| Peptide 29 | 18,643 | 3,087 | 6.04 | 35.15 |
| Peptide 30 | 205,442 | 63,394 | 3.24 | 320.95 |

Peptides 23, 25, 27 and 29 demonstrate a reduction in nectin-4 antibody binding compared to untreated control cells. Peptide 22 has increased nectin-4 antibody binding versus control. Peptide 30 results are erroneous/outlier due to solubility issues.

Effect of Nectin-1 Peptides on the Ability of a Monoclonal Antibody Against Nectin-4 to Bind to Ovarian Cancer Cells, as Determined by Flow Cytometry.

| Run Three Peptide Number | N4 MFI | IgG MFI | N4 MFI/ IgG MFI | [(Sn − Si)/ (Cn − Cl)] * 100 |
|---|---|---|---|---|
| Control 3 | 13,070.20 | 1330 | 9.83 | 100.00 |
| Peptide 31 | 15,498.21 | 1756 | 8.83 | 117.05 |
| Peptide 32 | 2,542.31 | 1029 | 2.47 | 12.89 |
| Peptide 33 | 10,425.01 | 1255 | 8.31 | 78.11 |
| Peptide 34 | 14,542.93 | 1489 | 9.77 | 111.19 |
| Peptide 35 | 15,767.33 | 1835 | 8.59 | 118.67 |
| Peptide 36 | 13,633.18 | 1748 | 7.80 | 101.23 |
| Peptide 37 | 46,393.69 | 4078 | 11.38 | 360.43 |
| Peptide 38 | 12,128.26 | 1568 | 7.73 | 89.95 |
| Peptide 39 | 8,719.33 | 2056 | 4.24 | 56.76 |
| Peptide 40 | 10,121.20 | 1423 | 7.11 | 74.09 |

Peptide 32 and 39 demonstrated a reduction in nectin-4 antibody binding compared to untreated control cells. Peptides 31, 34 and 35 appear to have increased nectin-4 antibody binding versus control.

| Run Four Peptide Number | N4 MFI | IgG MFI | N4 MFI/ IgG MFI | [(Sn − Si)/ (Cn − Cl)] * 100 |
|---|---|---|---|---|
| Control 4 | 9,631.58 | 1,026 | 9.387504873 | 100 |
| Peptide 41 | 9,040.73 | 1,089 | 8.301864096 | 92.40202287 |
| Peptide 42 | 9,416.50 | 1256 | 7.497213376 | 94.82800694 |
| Peptide 43 | 9,677.93 | 1308 | 7.399029052 | 97.26166046 |
| Peptide 44 | 7,802.22 | 920 | 8.480673913 | 79.9739239 |
| Peptide 45 | 9,868.29 | 1023 | 9.646422287 | 102.7855182 |
| Peptide 46 | 10,569.90 | 1596 | 6.622744361 | 104.2800137 |
| Peptide 47 | 11,949.18 | 1789 | 6.679250978 | 118.0650229 |
| Peptide 48 | 10,595.37 | 1069 | 9.911478017 | 110.699918 |
| Peptide 49 | 305,353.87 | 29486 | 10.35589331 | 3205.685962 |
| Peptide 50 | 11,341.38 | 2634 | 4.305763098 | 101.1829534 |

Peptides 41-50 show insignificant changes vs controls (excluding the erroneous/outlier peptide 49 results due to solubility issues).

| Run Five Peptide Number | N4 MFI | IgG MFI | N4 MFI/ IgG MFI | [(Sn − Si)/ (Cn − Cl)] * 100 |
|---|---|---|---|---|
| Control 5 | 17,768.90 | 8,294.87 | 2.142155332 | 100 |
| Peptide 51 | 14,202.55 | 9,230.44 | 1.538664462 | 52.48146776 |
| Peptide 52 | 20,692.13 | 7,617.02 | 2.716565008 | 138.0100126 |
| Peptide 53 | 40,909.47 | 29,864.47 | 1.369837469 | 116.5818559 |
| Peptide 54 | 19,706.27 | 8,747.26 | 2.252850607 | 115.6742168 |
| Peptide 55 | 19,498.24 | 8,512.75 | 2.290474876 | 115.9537177 |
| Peptide 56 | 21,060.14 | 10,346.61 | 2.035462823 | 113.0831336 |
| Peptide 57 | 14,705.92 | 7,848.89 | 1.873630539 | 72.37711935 |

Peptides 51 and 57 demonstrated a reduction in nectin-4 antibody binding compared to untreated control cells. Peptide 52 has increased nectin-4 antibody versus control.

Results from the Use of Scrambled Peptides to Block Cell Adhesion

Scrambled versions of some of the peptides that blocked cell adhesion were synthesized and then tested to see whether they would block cell adhesion. The data is presented in FIGS. 7-11, and shows that the functionally active peptides from Nectin-4 and Nectin-1 could block cell adhesion to Nectin-1 when tested at low concentrations, while the scrambled version of the same peptides required much higher concentrations to cause any blocking of cell adhesion. This shows that the amino acids in the proper sequences are necessary for functional activity.

Potential Therapeutic Applications:

Previous research has demonstrated the ability of cell surface ADAM molecules to cleave nectin 4 molecules from the surface of ovarian cancer cells. This cleavage process has consequences for the implementation of targeted therapies by reducing the amount of binding sites available to proposed drug-antibody conjugates. The flow cytometry data suggest that the synthetic peptides increase the affinity of nectin 4 antibodies for their target molecules. It is believed that this is due to blocking or reversing cleavage of nectin 4 from the cell surface. Furthermore, shed nectin 4 molecules present in the peritoneal cavity can reasonably be expected to bind to antibody-drug conjugates, thereby reducing the amount of drug available to cells. Synthetic peptides can be used prior to treatment to negate this "chaff" effect and allow for entry by the drug.

BIBLIOGRAPHY

Boylan et al. The expression of Nectin-4 on the surface of ovarian cancer cells alters their ability to adhere, migrate, aggregate and proliferate. Oncotarget. 2017 Feb. 7; 8(6); 9717-9738; published online 2016 Dec. 25.

Fabre-Lafay et al. Nectin-4 is a new histological and serological tumor associated marker for breast cancer. BMC Cancer. 2 May 2007. 7:23.

Buchanan et al. Ectodomain shedding of the cell adhesion molecule Nectin-4 in ovarian cancer is mediated by ADAM 10 and ADAM17. JBC 23 Feb. 2017.

Example III

Provided herein (FIGS. 12A and 12B) is data demonstrating that Nectin-4 and Nectin-1 peptides can inhibit ovarian cancer cell aggregation and spheroid formation when tested at t=24 hr and t=48 hr. The clinical relevance is that by blocking the formation of spheroids, the cells will be more sensitive to chemotherapy (which targets the single cells that proliferate more rapidly than spheroids).

The spheroid assay for peptides 1-30 were scored using a visual scale of +1 to +5. The controls were scored at +2 (24 hrs) and +4 (48 hrs). Using this semi-quantitative scale, 25 of the peptides reduced spheroid size at 48 hrs, but only 15 of these peptides had reduced spheroid size (relative to the control) at 24 hrs. It may be harder to visually assess the size at 24 hours, since the spheroids are relatively small, but and perhaps some of the peptides are affecting cell division, and that is why the spheroids are smaller than the controls at 48 hours, but not 24 hrs (this can be easily assayed with an MTT assay).

| Run One | | | | | | | | | | | | | |
|---|---|---|---|---|---|---|---|---|---|---|---|---|---|
| Paper ID | N4-P2 | N4-P3 | N4-P4 | N4-P5 | N4-P6 | N4-P7 | N4-P8 | N4-P9 | N4-P10 | N4-P11 | N4-P12 | N4-P13 | N4-P14 |
| Lab ID | 2 | 3 | 4 | 5 | 6 | 7 | 8 | 9 | 10 | 11 | 12 | 13 | 14 |
| Domain | IgV | IgV | IgV | IgV | IgV | IgV | IgV | IgV | IgV/ IgC1 | IgC1 | IgC1 | IgC1 | IgC1 |
| Inhibits Binding | X | X | | | X | | X | | X | | | | |
| Flow binding | | 37% | 49% | | | 128% | 137% | 50% | 12.50% | | | | |
| Spheroid-24- Control = 2 | | | 1 | | 1 | 3 | 3 | | 1 | 1? | | 1 | 1 |
| Spheroid-48 Control = 4 | 3 | 2 | 2 | 3 | 2 | | | 3 | 2 | 3 | | 2 | 2 |

-continued

| Paper ID | N4-P15 | N4-P16 | N4-P17 | N4-P18 | N4-P19 | N4-P20 | N4-P21 | N4-P22 | N4-P23 | N4-P24 |
|---|---|---|---|---|---|---|---|---|---|---|
| Lab ID | 15 | 16 | 17 | 18 | 19 | 20 | 21 | 22 | 23 | 24 |
| Domain | IgC1 | IgC1 | IgC1 | IgC1 | | IgC2 | IgC2 | IgC2 | IgC2 | IgC2 |
| Inhibits Binding | | | | XS | | | | XS | | |
| Flow binding | 44% | | | NR | 38% | 118% | | 143% | 35% | |
| Spheroid-24-Control = 2 | 1 | 1 | 1 | 3 | 1 | | 1 | 1 | 1 | |
| Spheroid-48 Control = 4 | 2 | 1 | 2 | 5 | 2 | 2 | 2 | 3 | 2 | 3 |

| Paper ID | N4-P25 | N4-P26 | N4-P27 | N4-P28 | N4-P29 | N1-P1 |
|---|---|---|---|---|---|---|
| Lab ID | 25 | 26 | 27 | 28 | 29 | 30 |
| Domain | IgC2 | IgC2 | | Adj Mem | IC | IgV |
| Inhibits Binding | | | | | XS | X |
| Flow binding | 9.40% | | 42% | | 35% | 321% |
| Spheroid-24- Control = 2 | 2 | 1 | 1 | | 3 | |
| Spheroid-48 Control = 4 | | 2 | 2 | 2 | | 3 |

Run Two

| Paper ID | N1-P2 | N1-P3 | N1-P4 | N1-P5 | N1-P6 | N1-P7 | N1-P8 | N1-P9 | N1-P10 | N1-P11 | N1-P12 | N1-P13 |
|---|---|---|---|---|---|---|---|---|---|---|---|---|
| Lab ID | 31 | 32 | 33 | 34 | 35 | 36 | 37 | 38 | 39 | 40 | 41 | 42 |
| Domain | IgV | IgV | IgV | IgV | IgV | IgV | IgV | IgV | IgV | IgC1 | IgC1 | IgC1 |
| Inhibits Binding | | | | | | | X | | X | | | |
| Flow binding | 117% | 13% | | 112% | 119% | | | | 57% | | | |
| Spheroid-24-Control = 2 | NS | | | | | | | 1 | | | 3 | |
| Spheroid-48 Control = 4 | NS | 2 | | | 3 | | | 3 | | | | |

NS = Not Scoreable

| Paper ID | N1-P14 | N1-P15 | N1-P16 | N1-P17 | N1-P18 | N1-P19 | N1-P20 | N1-P21 | N1-P22 |
|---|---|---|---|---|---|---|---|---|---|
| Lab ID | 43 | 44 | 45 | 46 | 47 | 48 | 49 | 50 | 51 |
| Domain | IgC1 | IgC1 | IgC1 | IgC1 | IgC2 | IgC2 | IgC2 | IgC2 | IgC2 |
| Inhibits Binding | | | | XS | | | XS | | |
| Flow binding | 3 | | | | | | | | 53% |
| Spheroid-24-Control = 2 | 5 | 3 | 3 | | 1 | 1 | NS | | |
| Spheroid-48 Control = 4 | | | | | 2 | 2 | NS | | |

NS = Not Scoreable

| Paper ID | N1-P23 | N1-P24 | N1-P25 | N1-P26 | N1-P27 | N1-P28 |
|---|---|---|---|---|---|---|
| Lab ID | 52 | 53 | 54 | 55 | 56 | 57 |
| Domain | IgC2 | IgC2 | IgC2 | IgC2 | | |
| Inhibits Binding | | X | X | X | | |
| Flow binding | 138% | | | | | |
| Spheroid-24-Control = 2 | 1 | | | | | |
| Spheroid-48 Control = 4 | 2 | | | | 3 | 3 |

NS = Not Scoreable

Figure 12A:
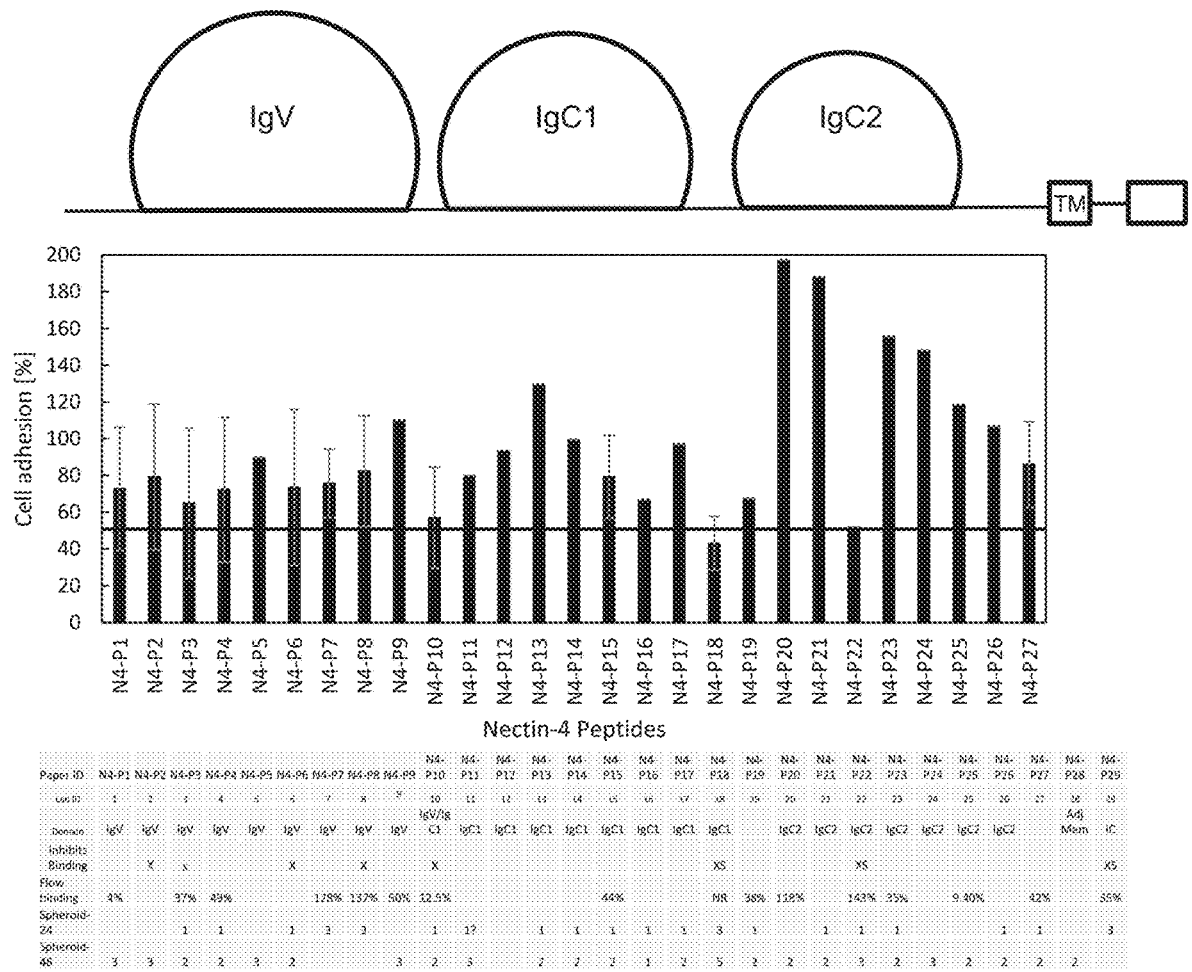
Figure 12B:
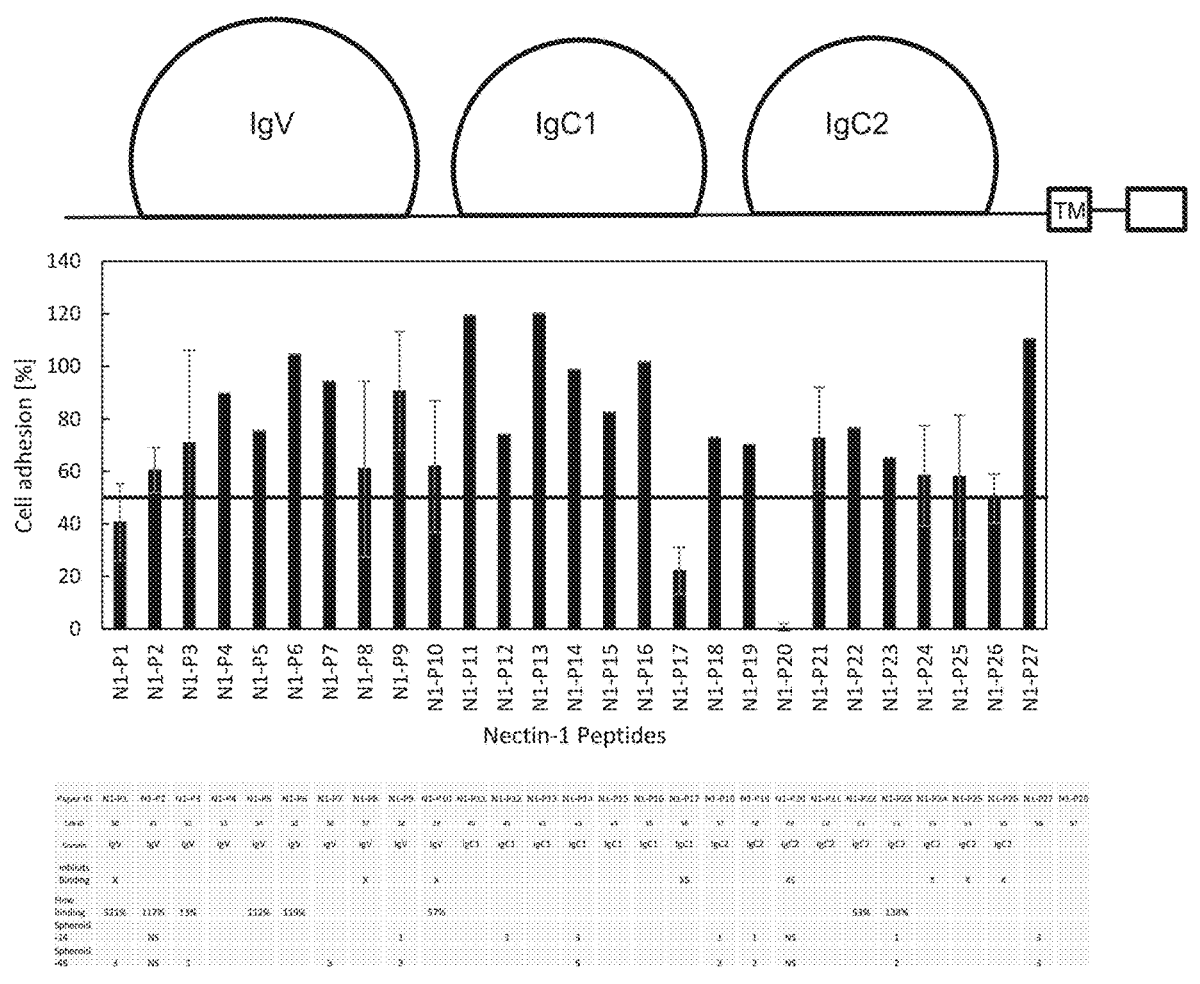

FIGS. 12A-B provide a summary of peptide binding assay data (binding, flow and spheroid formation) for Nectin-4 and Nectin-1. For example, peptides 7 and 8 increased the binding of the Nectin-4 antibody to cells as determined by flow cytometry, and also caused slightly larger spheroid size at 24 hrs. And peptides 10, 15 and 19 reduced antibody binding and also reduced spheroid size at both 24 and 28 hours.

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

What is claimed is:

1. A peptide selected from the group consisting of N4-P1 to N4-P28 (SEQ ID NOs: 5-31 and 59) and N1-P1 to N1-P27 (SEQ ID NOs: 32-58).

2. The peptide of claim 1, wherein the peptide is N4-P10, N4-P18, N4-P22, N1-P1, N1-P17, N1-P20 or N1-P26.

3. A composition comprising at least one peptide according to claim 1 and a pharmaceutically acceptable carrier.

4. The composition of claim 3, comprising 2, 3, 4, 5, 6, 7, 8, 9 or 10 peptides according to claim 1.

5. A peptide selected from the group consisting of N4-P10, N4-P18, N4-P22, N1-P1, N1-P17, N1-P20 and N1-P26.

6. A method to inhibit cell adhesion of an ovarian cancer cell comprising contacting said cancer cell with an effective amount of at least one peptide of claim 2.

7. A method to inhibit spheroid formation of an ovarian cancer cell comprising contacting said cancer cell with an effective amount of at least one peptide selected from the group consisting of N4-P10, N4-P22 and N4-P27.

8. A method to inhibit cell adhesion of an ovarian cancer cell comprising administering to a subject in need thereof an effective amount of at least one peptide of claim 2.

9. The method of claim 8, wherein the cell adhesion is an intraperitoneal adhesion following surgery.

10. A method to treat ovarian cancer comprising administering to a subject in need thereof an effective amount of at least one peptide of claim 2.

* * * * *

UNITED STATES PATENT AND TRADEMARK OFFICE
CERTIFICATE OF CORRECTION

PATENT NO. : 10,907,212 B2
APPLICATION NO. : 15/595604
DATED : February 2, 2021
INVENTOR(S) : Skubitz et al.

It is certified that error appears in the above-identified patent and that said Letters Patent is hereby corrected as shown below:

In the Specification

In Column 2, Line 33, delete "Nectin-4," and insert --Nectin-4 (N4),-- therefor

In Column 2, Line 34, after "Nectin-1", insert --(N1)--

In Column 3, Line 65, delete "peptide," and insert --peptide-- therefor

In Column 7, Line 53, delete "Gin;" and insert --Gln;-- therefor

In Column 9, Line 31, delete "C1-10" and insert --$C_{1-10}$-- therefor

In Column 9, Line 44, delete "2', -3',- or 4'-methyl-2," and insert --2'-, 3'-, or 4'-methyl-2,-- therefor In Column 9, Line 53, delete "example." and insert --example).-- therefor In Column 12, Line 21, delete "C1-C5" and insert --$C_1$-$C_5$-- therefor In Column 12, Line 32, delete "(-NH2)," and insert --(-NH$_2$),-- therefor In Column 23, Line 25, delete "V A)." and insert --VA).-- therefor In Column 23, Line 47, delete "µs/ml" and insert --µg/ml-- therefor In Column 24, Line 7, delete "Ibidi®" and insert --ibidi®-- therefor In Column 24, Line 8, delete "(Ibidi®," and insert --(ibidi®,-- therefor Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,907,212 B2

In Column 32, Line 47, delete "Braun O," and insert --Braun CJ,-- therefor

In Column 36, Line 26, delete "ADAM 10" and insert --ADAM10-- therefor

SEQUENCE LISTING

```
<160> NUMBER OF SEQ ID NOS: 61

<210> SEQ ID NO 1
<211> LENGTH: 20
<212> TYPE: DNA
<213> ORGANISM: Artificial Sequence
<220> FEATURE:
<223> OTHER INFORMATION: A synthetic primer

<400> SEQUENCE: 1
caaaatctgt ggcacattgg                                                  20

<210> SEQ ID NO 2
<211> LENGTH: 20
<212> TYPE: DNA
<213> ORGANISM: Artificial Sequence
<220> FEATURE:
<223> OTHER INFORMATION: A synthetic primer

<400> SEQUENCE: 2
gctgacatgg cagacgtaga                                                  20

<210> SEQ ID NO 3
<211> LENGTH: 20
<212> TYPE: DNA
<213> ORGANISM: Artificial Sequence
<220> FEATURE:
<223> OTHER INFORMATION: A synthetic primer

<400> SEQUENCE: 3
accacagtcc atgccatcac                                                  20

<210> SEQ ID NO 4
<211> LENGTH: 20
<212> TYPE: DNA
<213> ORGANISM: Artificial Sequence
<220> FEATURE:
<223> OTHER INFORMATION: A synthetic primer

<400> SEQUENCE: 4
tccaccaccc tgttgctgta                                                  20

<210> SEQ ID NO 5
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 5

Pro Ala Gly Glu Leu Glu Thr Ser Asp Val Val Thr Val Val
1               5                   10

<210> SEQ ID NO 6
<211> LENGTH: 14
```

-continued

```
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 6

Val Val Leu Gly Gln Asp Ala Lys Leu Pro Cys Phe Tyr Arg
1               5                   10

<210> SEQ ID NO 7
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 7

Tyr Arg Gly Asp Ser Gly Glu Gln Val Gly Gln Val Ala Trp
1               5                   10

<210> SEQ ID NO 8
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 8

Ala Trp Ala Arg Val Asp Ala Gly Glu Gly Ala Gln Glu Leu
1               5                   10

<210> SEQ ID NO 9
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 9

Glu Leu Ala Leu Leu His Ser Lys Tyr Gly Leu His Val Ser
1               5                   10

<210> SEQ ID NO 10
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 10

Val Ser Pro Ala Tyr Glu Gly Arg Val Glu Gln Pro Pro Pro
1               5                   10

<210> SEQ ID NO 11
<211> LENGTH: 14
<212> TYPE: PRT
<213> ORGANISM: Homo sapiens
<220> FEATURE:
<221> NAME/KEY: AMIDATION
```

-continued

```
<222> LOCATION: 14
<223> OTHER INFORMATION: a c-terminal carboxamide (-NH2)

<400> SEQUENCE: 11

Pro Pro Pro Arg Asn Pro Leu Asp Gly Ser Val Leu Leu Arg
1               5                   10

<210> SEQ ID NO 12
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 12

Leu Arg Asn Ala Val Gln Ala Asp Glu Gly Glu Tyr Glu Cys
1               5                   10

<210> SEQ ID NO 13
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 13

Glu Cys Arg Val Ser Thr Phe Pro Ala Gly Ser Phe Gln Ala
1               5                   10

<210> SEQ ID NO 14
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 14

Gln Ala Arg Leu Arg Leu Arg Val Leu Val Pro Pro Leu Pro
1               5                   10

<210> SEQ ID NO 15
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 15

Leu Pro Ser Leu Asn Pro Gly Pro Ala Leu Glu Glu Gly Gln
1               5                   10

<210> SEQ ID NO 16
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 16
```

Gly Gln Gly Leu Thr Leu Ala Ala Ser Cys Thr Ala Glu Gly
1               5                   10

<210> SEQ ID NO 17
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 17

Glu Gly Ser Pro Ala Pro Ser Val Thr Trp Asp Thr Glu Val
1               5                   10

<210> SEQ ID NO 18
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 18

Glu Val Lys Gly Thr Thr Ser Ser Arg Ser Phe Lys His Ser
1               5                   10

<210> SEQ ID NO 19
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 19

His Ser Arg Ser Ala Ala Val Thr Ser Glu Phe His Leu Val
1               5                   10

<210> SEQ ID NO 20
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 20

Leu Val Pro Ser Arg Ser Met Asn Gly Gln Pro Leu Thr Cys
1               5                   10

<210> SEQ ID NO 21
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 21

Thr Cys Val Val Ser His Pro Gly Leu Leu Gln Asp Gln Arg
1               5                   10

-continued

```
<210> SEQ ID NO 22
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 22

Gln Arg Ile Thr His Ile Leu His Val Ser Phe Leu Ala Glu
1               5                   10

<210> SEQ ID NO 23
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 23

Ala Glu Ala Ser Val Arg Gly Leu Glu Asp Gln Asn Leu Trp
1               5                   10

<210> SEQ ID NO 24
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 24

Leu Trp His Ile Gly Arg Glu Gly Ala Met Leu Lys Cys Leu
1               5                   10

<210> SEQ ID NO 25
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 25

Cys Leu Ser Glu Gly Gln Pro Pro Pro Ser Tyr Asn Trp Thr
1               5                   10

<210> SEQ ID NO 26
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 26

Trp Thr Arg Leu Asp Gly Pro Leu Pro Ser Gly Val Arg Val
1               5                   10

<210> SEQ ID NO 27
<211> LENGTH: 14
<212> TYPE: PRT
```

```
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 27

Arg Val Asp Gly Asp Thr Leu Gly Phe Pro Pro Leu Thr Thr
1               5                   10

<210> SEQ ID NO 28
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 28

Thr Thr Glu His Ser Gly Ile Tyr Val Cys His Val Ser Asn
1               5                   10

<210> SEQ ID NO 29
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 29

Ser Asn Glu Phe Ser Ser Arg Asp Ser Gln Val Thr Val Asp
1               5                   10

<210> SEQ ID NO 30
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 30

Val Asp Val Leu Asp Pro Gln Glu Asp Ser Gly Lys Gln Val
1               5                   10

<210> SEQ ID NO 31
<211> LENGTH: 11
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 31

Ser Gly Lys Gln Val Asp Leu Val Ser Ala Ser
1               5                   10

<210> SEQ ID NO 32
<211> LENGTH: 14
<212> TYPE: PRT
<213> ORGANISM: Homo sapiens
<220> FEATURE:
<221> NAME/KEY: AMIDATION
<222> LOCATION: 14
```

<223> OTHER INFORMATION: a c-terminal carboxamide (-NH2)

<400> SEQUENCE: 32

His Ser Gln Val Val Gln Val Asn Asp Ser Met Tyr Gly Phe
1               5                   10

<210> SEQ ID NO 33
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 33

Gly Phe Ile Gly Thr Asp Val Val Leu His Cys Ser Phe Ala
1               5                   10

<210> SEQ ID NO 34
<211> LENGTH: 15
<212> TYPE: PRT
<213> ORGANISM: Homo sapiens
<220> FEATURE:
<221> NAME/KEY: AMIDATION
<222> LOCATION: 15
<223> OTHER INFORMATION: a c-terminal carboxamide (-NH2)

<400> SEQUENCE: 34

Phe Ala Asn Pro Leu Pro Ser Val Lys Ile Thr Gln Val Thr Trp
1               5                   10                  15

<210> SEQ ID NO 35
<211> LENGTH: 13
<212> TYPE: PRT
<213> ORGANISM: Homo sapiens
<220> FEATURE:
<221> NAME/KEY: AMIDATION
<222> LOCATION: 13
<223> OTHER INFORMATION: a c-terminal carboxamide (-NH2)

<400> SEQUENCE: 35

Thr Trp Gln Lys Ser Thr Asn Gly Ser Lys Gln Asn Val
1               5                   10

<210> SEQ ID NO 36
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 36

Asn Val Ala Ile Tyr Asn Pro Ser Met Gly Val Ser Val Leu
1               5                   10

<210> SEQ ID NO 37
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 37

```
Val Leu Ala Pro Tyr Arg Glu Arg Val Glu Phe Leu Arg Pro
1               5                   10
```

<210> SEQ ID NO 38
<211> LENGTH: 12
<212> TYPE: PRT
<213> ORGANISM: Homo sapiens
<220> FEATURE:
<221> NAME/KEY: AMIDATION
<222> LOCATION: 12
<223> OTHER INFORMATION: a c-terminal carboxamide (-NH2)

<400> SEQUENCE: 38

```
Arg Pro Ser Phe Thr Asp Gly Thr Ile Arg Leu Ser
1               5                   10
```

<210> SEQ ID NO 39
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 39

```
Leu Ser Arg Leu Glu Leu Glu Asp Glu Gly Val Tyr Ile Cys
1               5                   10
```

<210> SEQ ID NO 40
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 40

```
Ile Cys Glu Phe Ala Thr Phe Pro Thr Gly Asn Arg Glu Ser
1               5                   10
```

<210> SEQ ID NO 41
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 41

```
Glu Ser Gln Leu Asn Leu Thr Val Met Ala Lys Pro Thr Asn
1               5                   10
```

<210> SEQ ID NO 42
<211> LENGTH: 17
<212> TYPE: PRT
<213> ORGANISM: Homo sapiens
<220> FEATURE:
<221> NAME/KEY: AMIDATION
<222> LOCATION: 17
<223> OTHER INFORMATION: a c-terminal carboxamide (-NH2)

<400> SEQUENCE: 42

```
Thr Asn Trp Ile Glu Gly Thr Gln Ala Val Leu Arg Ala Lys Lys Gly
1               5                   10                  15

Gln
```

```
<210> SEQ ID NO 43
<211> LENGTH: 16
<212> TYPE: PRT
<213> ORGANISM: Homo sapiens
<220> FEATURE:
<221> NAME/KEY: AMIDATION
<222> LOCATION: 16
<223> OTHER INFORMATION: a c-terminal carboxamide (-NH2)

<400> SEQUENCE: 43

Gly Gln Asp Asp Lys Val Leu Val Ala Thr Cys Thr Ser Ala Asn Gly
1               5                   10                  15

<210> SEQ ID NO 44
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 44

Asn Gly Lys Pro Pro Ser Val Val Ser Trp Glu Thr Arg Leu
1               5                   10

<210> SEQ ID NO 45
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 45

Arg Leu Lys Gly Glu Ala Glu Tyr Gln Glu Ile Arg Asn Pro
1               5                   10

<210> SEQ ID NO 46
<211> LENGTH: 15
<212> TYPE: PRT
<213> ORGANISM: Homo sapiens
<220> FEATURE:
<221> NAME/KEY: AMIDATION
<222> LOCATION: 15
<223> OTHER INFORMATION: a c-terminal carboxamide (-NH2)

<400> SEQUENCE: 46

Asn Pro Asn Gly Thr Val Thr Val Ile Ser Arg Tyr Arg Leu Val
1               5                   10                  15

<210> SEQ ID NO 47
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 47

Leu Val Pro Ser Arg Glu Ala His Gln Gln Ser Leu Ala Cys
1               5                   10

<210> SEQ ID NO 48
<211> LENGTH: 14
```

```
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 48

Ala Cys Ile Val Asn Tyr His Met Asp Arg Phe Lys Glu Ser
1               5                   10

<210> SEQ ID NO 49
<211> LENGTH: 12
<212> TYPE: PRT
<213> ORGANISM: Homo sapiens
<220> FEATURE:
<221> NAME/KEY: AMIDATION
<222> LOCATION: 12
<223> OTHER INFORMATION: a c-terminal carboxamide (-NH2)

<400> SEQUENCE: 49

Glu Ser Leu Thr Leu Asn Val Gln Tyr Glu Pro Glu
1               5                   10

<210> SEQ ID NO 50
<211> LENGTH: 12
<212> TYPE: PRT
<213> ORGANISM: Homo sapiens
<220> FEATURE:
<221> NAME/KEY: AMIDATION
<222> LOCATION: 12
<223> OTHER INFORMATION: a c-terminal carboxamide (-NH2)

<400> SEQUENCE: 50

Pro Glu Val Thr Ile Glu Gly Phe Asp Gly Asn Trp
1               5                   10

<210> SEQ ID NO 51
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 51

Asn Trp Tyr Leu Gln Arg Met Asp Val Lys Leu Thr Cys Lys
1               5                   10

<210> SEQ ID NO 52
<211> LENGTH: 15
<212> TYPE: PRT
<213> ORGANISM: Homo sapiens
<220> FEATURE:
<221> NAME/KEY: AMIDATION
<222> LOCATION: 15
<223> OTHER INFORMATION: a c-terminal carboxamide (-NH2)

<400> SEQUENCE: 52

Cys Lys Ala Asp Ala Asn Pro Pro Ala Thr Glu Tyr His Trp Thr
1               5                   10                  15

<210> SEQ ID NO 53
<211> LENGTH: 14
<212> TYPE: PRT
<213> ORGANISM: Homo sapiens
<220> FEATURE:
<221> NAME/KEY: AMIDATION
```

```
<222> LOCATION: 14
<223> OTHER INFORMATION: a c-terminal carboxamide (-NH2)

<400> SEQUENCE: 53

Trp Thr Thr Leu Asn Gly Ser Leu Pro Lys Gly Val Glu Ala
1               5                   10

<210> SEQ ID NO 54
<211> LENGTH: 15
<212> TYPE: PRT
<213> ORGANISM: Homo sapiens
<220> FEATURE:
<221> NAME/KEY: AMIDATION
<222> LOCATION: 15
<223> OTHER INFORMATION: a c-terminal carboxamide (-NH2)

<400> SEQUENCE: 54

Glu Ala Gln Asn Arg Thr Leu Phe Phe Lys Gly Pro Ile Asn Tyr
1               5                   10                  15

<210> SEQ ID NO 55
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 55

Asn Tyr Ser Leu Ala Gly Thr Tyr Ile Cys Glu Ala Thr Asn
1               5                   10

<210> SEQ ID NO 56
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 56

Thr Asn Pro Ile Gly Thr Arg Ser Gly Gln Val Glu Val Asn
1               5                   10

<210> SEQ ID NO 57
<211> LENGTH: 19
<212> TYPE: PRT
<213> ORGANISM: Homo sapiens
<220> FEATURE:
<221> NAME/KEY: AMIDATION
<222> LOCATION: 19
<223> OTHER INFORMATION: a c-terminal carboxamide (-NH2)

<400> SEQUENCE: 57

Val Asn Ile Thr Glu Phe Pro Tyr Thr Pro Ser Pro Pro Glu His Gly
1               5                   10                  15

Arg Arg Ala

<210> SEQ ID NO 58
<211> LENGTH: 11
<212> TYPE: PRT
<213> ORGANISM: Homo sapiens
<220> FEATURE:
<221> NAME/KEY: AMIDATION
<222> LOCATION: 11
<223> OTHER INFORMATION: a c-terminal carboxamide (-NH2)
```

```
<400> SEQUENCE: 58

His Gly Arg Arg Ala Gly Pro Val Pro Thr Ala
1               5                   10

<210> SEQ ID NO 59
<211> LENGTH: 18
<212> TYPE: PRT
<213> ORGANISM: Homo sapiens
<220> FEATURE:
<221> NAME/KEY: AMIDATION
<222> LOCATION: 18
<223> OTHER INFORMATION: a c-terminal carboxamide (-NH2)

<400> SEQUENCE: 59

Trp Thr Arg Leu Asp Gly Pro Leu Pro Ser Gly Val Arg Val Asp Gly
1               5                   10                  15

Asp Thr

<210> SEQ ID NO 60
<211> LENGTH: 14
<212> TYPE: PRT
<213> ORGANISM: Homo sapiens
<220> FEATURE:
<221> NAME/KEY: AMIDATION
<222> LOCATION: 14
<223> OTHER INFORMATION: a c-terminal carboxamide (-NH2)

<400> SEQUENCE: 60

Thr Gly Asn Gly Ile Tyr Ile Asn Gly Arg Gly His Leu Val
1               5                   10

<210> SEQ ID NO 61
<211> LENGTH: 18
<212> TYPE: PRT
<213> ORGANISM: Homo sapiens
<220> FEATURE:
<221> NAME/KEY: AMIDATION
<222> LOCATION: 18
<223> OTHER INFORMATION: a c-terminal carboxamide (-NH2)

<400> SEQUENCE: 61

Trp Thr Thr Leu Asn Gly Ser Leu Pro Lys Gly Val Glu Ala Gln Asn
1               5                   10                  15

Arg Thr
```